United States Patent
Saadat et al.

(10) Patent No.: US 7,637,905 B2
(45) Date of Patent: Dec. 29, 2009

(54) ENDOLUMINAL TOOL DEPLOYMENT SYSTEM

(75) Inventors: Vahid Saadat, Atherton, CA (US);
Richard C. Ewers, Fullerton, CA (US);
Eugene G. Chen, Carlsbad, CA (US);
David Miller, Cupertino, CA (US)

(73) Assignee: USGI Medical, Inc., San Clemente, CA (US)

( * ) Notice: Subject to any disclaimer, the term of this patent is extended or adjusted under 35 U.S.C. 154(b) by 0 days.

(21) Appl. No.: 10/346,709

(22) Filed: Jan. 15, 2003

(65) Prior Publication Data
US 2004/0138525 A1    Jul. 15, 2004

(51) Int. Cl.
*A61B 17/00*    (2006.01)
*A61B 1/00*    (2006.01)

(52) U.S. Cl. .................. 606/1; 600/104; 600/142

(58) Field of Classification Search ............... 600/104, 600/139, 141, 142, 149, 114, 146; 606/45, 606/1; 623/62
See application file for complete search history.

(56) References Cited

U.S. PATENT DOCUMENTS

| | | | |
|---|---|---|---|
| 616,672 A | 12/1898 | Kelling | |
| 2,510,198 A | 6/1950 | Tesmer | |
| 2,533,494 A | 12/1950 | Mitchell, Jr. | |
| 3,060,972 A | 10/1962 | Sheldon | |
| 3,096,962 A | 7/1963 | Meijs | |
| 3,162,214 A | 12/1964 | Bazinet, Jr. | |
| 3,168,274 A | 2/1965 | Street | |
| 3,266,059 A * | 8/1966 | Stelle ..................... | 623/62 |
| 3,430,662 A | 3/1969 | Guamaschelli | |
| 3,546,961 A | 12/1970 | Marton | |
| 3,583,393 A * | 6/1971 | Takahashi ............... | 600/142 |
| 3,858,578 A | 1/1975 | Milo | |
| 3,913,565 A | 10/1975 | Kawahara | |
| 3,915,157 A | 10/1975 | Mitsui | |
| 3,948,251 A | 4/1976 | Hosono | |
| 4,036,218 A | 7/1977 | Yamashita et al. | |
| 4,054,128 A | 10/1977 | Seufert et al. | |
| 4,201,198 A | 5/1980 | Okada et al. | |
| 4,224,929 A | 9/1980 | Furihata | |
| 4,245,624 A | 1/1981 | Komiya | |

(Continued)

FOREIGN PATENT DOCUMENTS

DE    3504824    *    8/1986

(Continued)

*Primary Examiner*—Julian W Woo
(74) *Attorney, Agent, or Firm*—Levine Bagade Han LLP; Charles C. Fowler

(57) ABSTRACT

Systems, devices and methods are provided for endoscopic procedures involving tissue manipulations beyond the capabilities of traditional endoscopic instruments. Embodiments of the systems include an elongated main body having a scope therethrough and at least one steerable tool arm which extends from the distal end of the main body. In preferred embodiments, the system includes two tool arms, each arm steerable to form a curve laterally outward which then bends laterally inward so that the arms form an angular shape. In addition, end effectors extend from the distal ends of each tool arm for use in manipulation of tissue. The angular shape brings the end effectors together in view of the scope for cooperative movements which are continuously visible by the surgeon. In addition, the tool arms may be steerable in any additional direction and may be rotatable to allow grasping, elevation and more complex manipulation of tissue.

20 Claims, 27 Drawing Sheets

U.S. PATENT DOCUMENTS

| | | | |
|---|---|---|---|
| 4,366,810 A | 1/1983 | Slanetz, Jr. | |
| 4,648,733 A | 3/1987 | Merkt | |
| 4,651,718 A * | 3/1987 | Collins et al. | 600/142 |
| 4,655,257 A | 4/1987 | Iwashita | |
| 4,700,693 A * | 10/1987 | Lia et al. | 600/141 |
| 4,949,927 A | 8/1990 | Madocks et al. | |
| 4,988,171 A | 1/1991 | Yokota | |
| 5,000,683 A | 3/1991 | Brock | |
| 5,015,249 A | 5/1991 | Nakab et al. | |
| 5,020,539 A | 6/1991 | Yokoi et al. | |
| 5,035,231 A | 7/1991 | Kubokawa et al. | |
| 5,068,719 A | 11/1991 | Tsuji | |
| 5,088,979 A | 2/1992 | Filipi et al. | |
| 5,099,827 A * | 3/1992 | Melzer et al. | 600/104 |
| 5,170,775 A | 12/1992 | Tagami | |
| 5,172,225 A | 12/1992 | Takahashi | |
| 5,187,572 A | 2/1993 | Nakamura et al. | |
| 5,196,928 A | 3/1993 | Karasawa et al. | |
| 5,251,611 A | 10/1993 | Zehel et al. | |
| 5,275,608 A | 1/1994 | Forman et al. | |
| 5,318,528 A | 6/1994 | Heaven et al. | |
| 5,337,732 A | 8/1994 | Grundfest et al. | |
| 5,337,733 A | 8/1994 | Bauerfeind et al. | |
| 5,348,259 A | 9/1994 | Blanco et al. | |
| 5,395,367 A * | 3/1995 | Wilk | 606/1 |
| 5,397,304 A | 3/1995 | Truckai | |
| 5,403,326 A | 4/1995 | Harrison et al. | |
| 5,441,499 A * | 8/1995 | Fritzsch | 606/45 |
| 5,448,989 A * | 9/1995 | Heckele | 600/142 |
| 5,558,665 A | 9/1996 | Kieturakis | |
| 5,624,380 A * | 4/1997 | Takayama et al. | 600/146 |
| 5,624,381 A | 4/1997 | Kieturakis | |
| 5,662,587 A | 9/1997 | Grundfest et al. | |
| 5,704,898 A | 1/1998 | Kokish | |
| 5,749,828 A | 5/1998 | Solomon et al. | |
| 5,759,151 A | 6/1998 | Sturges | |
| 5,766,169 A | 6/1998 | Fritzsch et al. | |
| 5,772,597 A | 6/1998 | Goldberger et al. | |
| 5,897,417 A | 4/1999 | Grey | |
| 5,902,254 A | 5/1999 | Magram | |
| 5,904,647 A * | 5/1999 | Ouchi | 600/104 |
| 5,908,381 A * | 6/1999 | Aznoian et al. | 600/104 |
| 5,916,147 A | 6/1999 | Boury | |
| 5,921,915 A | 7/1999 | Azonian et al. | |
| 5,928,264 A | 7/1999 | Sugarbaker et al. | |
| 5,954,731 A | 9/1999 | Yoon | |
| 5,954,733 A | 9/1999 | Yoon | |
| 5,957,937 A | 9/1999 | Yoon | |
| 5,984,932 A | 11/1999 | Yoon | |
| 5,993,466 A | 11/1999 | Yoon | |
| 5,993,467 A | 11/1999 | Yoon | |
| 6,017,358 A | 1/2000 | Yoon et al. | |
| 6,042,155 A | 3/2000 | Lockwood | |
| 6,086,601 A | 7/2000 | Yoon | |
| 6,159,146 A | 12/2000 | El Gayerli | |
| 6,159,224 A | 12/2000 | Yoon | |
| 6,174,280 B1 | 1/2001 | Oneda et al. | |
| 6,179,776 B1 | 1/2001 | Adams et al. | |
| 6,197,017 B1 | 3/2001 | Brock et al. | |
| 6,277,064 B1 | 8/2001 | Yoon | |
| 6,331,165 B1 | 12/2001 | Turturro et al. | |
| 6,352,503 B1 | 3/2002 | Matsui et al. | |
| 6,425,859 B1 | 7/2002 | Foley et al. | |
| 6,428,468 B1 | 8/2002 | Knighton et al. | |
| 6,432,112 B2 | 8/2002 | Brock et al. | |
| 6,443,944 B1 | 9/2002 | Doshi et al. | |
| 6,458,074 B1 | 10/2002 | Matsui et al. | |
| 6,468,203 B2 * | 10/2002 | Belson | 600/146 |
| 6,478,791 B1 | 11/2002 | Carter et al. | |
| 6,494,888 B1 | 12/2002 | Laufer et al. | |
| 6,506,196 B1 | 1/2003 | Laufer et al. | |
| 6,527,753 B2 * | 3/2003 | Sekine et al. | 600/104 |
| 6,554,793 B1 | 4/2003 | Pauker et al. | |
| 6,663,639 B1 | 12/2003 | Laufer et al. | |
| 6,743,240 B2 | 6/2004 | Smith et al. | |
| 6,761,685 B2 | 7/2004 | Adams et al. | |
| 6,773,441 B1 | 8/2004 | Laufer et al. | |
| 6,800,056 B2 * | 10/2004 | Tartaglia et al. | 600/114 |
| 6,811,532 B2 | 11/2004 | Ogura et al. | |
| 6,821,285 B2 | 11/2004 | Laufer et al. | |
| 6,835,199 B2 | 12/2004 | McGuckin, Jr. et al. | |
| 6,837,846 B2 * | 1/2005 | Jaffe et al. | 600/114 |
| 6,837,849 B2 | 1/2005 | Ogura et al. | |
| 6,899,673 B2 | 5/2005 | Ogura et al. | |
| 2001/0000040 A1 | 3/2001 | Adams et al. | |
| 2002/0062062 A1 | 5/2002 | Belson et al. | |
| 2002/0087048 A1 | 7/2002 | Brock et al. | |
| 2002/0120178 A1 | 8/2002 | Tartaglia et al. | |
| 2002/0120253 A1 | 8/2002 | Ouchi | |
| 2002/0147385 A1 | 10/2002 | Butler et al. | |
| 2002/0161281 A1 | 10/2002 | Jaffe et al. | |
| 2002/0193661 A1 | 12/2002 | Belson | |
| 2002/0193662 A1 | 12/2002 | Belson | |
| 2002/0193816 A1 | 12/2002 | Laufer et al. | |
| 2003/0045778 A1 | 3/2003 | Ohline et al. | |
| 2003/0181924 A1 | 9/2003 | Yamamoto et al. | |
| 2003/0236505 A1 | 12/2003 | Bonadio et al. | |
| 2003/0236549 A1 | 12/2003 | Bonadio et al. | |
| 2004/0010271 A1 | 1/2004 | Kortenbach | |
| 2004/0024386 A1 | 2/2004 | Deem et al. | |
| 2004/0059350 A1 | 3/2004 | Gordan et al. | |
| 2004/0193008 A1 | 9/2004 | Jaffe et al. | |
| 2004/0193009 A1 | 9/2004 | Jaffe et al. | |
| 2004/0193117 A1 | 9/2004 | Laufer et al. | |
| 2004/0193184 A1 | 9/2004 | Laufer et al. | |
| 2004/0193193 A1 | 9/2004 | Laufer et al. | |
| 2004/0193194 A1 | 9/2004 | Laufer et al. | |
| 2004/0194790 A1 | 10/2004 | Laufer et al. | |
| 2005/0020901 A1 | 1/2005 | Belson et al. | |
| 2005/0043758 A1 | 2/2005 | Golden et al. | |
| 2005/0049617 A1 | 3/2005 | Chatlynne et al. | |
| 2005/0119524 A1 | 6/2005 | Sekine et al. | |
| 2005/0267335 A1 | 12/2005 | Okada et al. | |

FOREIGN PATENT DOCUMENTS

| | | |
|---|---|---|
| DE | 3504824 A1 | 8/1986 |
| EP | 0 497 781 B1 | 8/1992 |
| JP | 54-136780 | 10/1979 |
| JP | 06-054796 A | 3/1994 |
| WO | WO 99/51283 A2 | 10/1999 |
| WO | WO 99/59664 A1 | 11/1999 |
| WO | WO 00/54653 A1 | 9/2000 |
| WO | WO 01/70096 A1 | 9/2001 |
| WO | WO 01/70097 A1 | 9/2001 |
| WO | WO 02/069841 A2 | 9/2002 |
| WO | WO 02/074178 | 9/2002 |
| WO | WO 03/092509 A1 | 11/2003 |
| WO | WO 03/105732 A1 | 12/2003 |
| WO | WO 2004/019788 A2 | 3/2004 |
| WO | WO 2004/049905 A2 | 6/2004 |
| WO | WO 2004/071284 A1 | 8/2004 |
| WO | WO 2004/103189 A1 | 12/2004 |
| WO | WO 2005/053517 A1 | 6/2005 |

\* cited by examiner

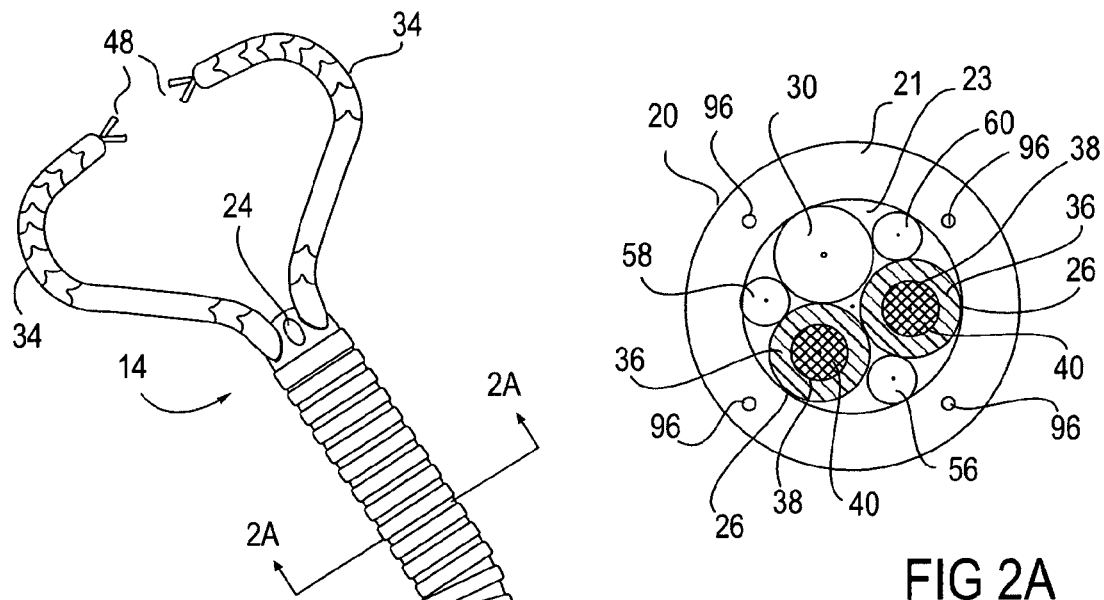
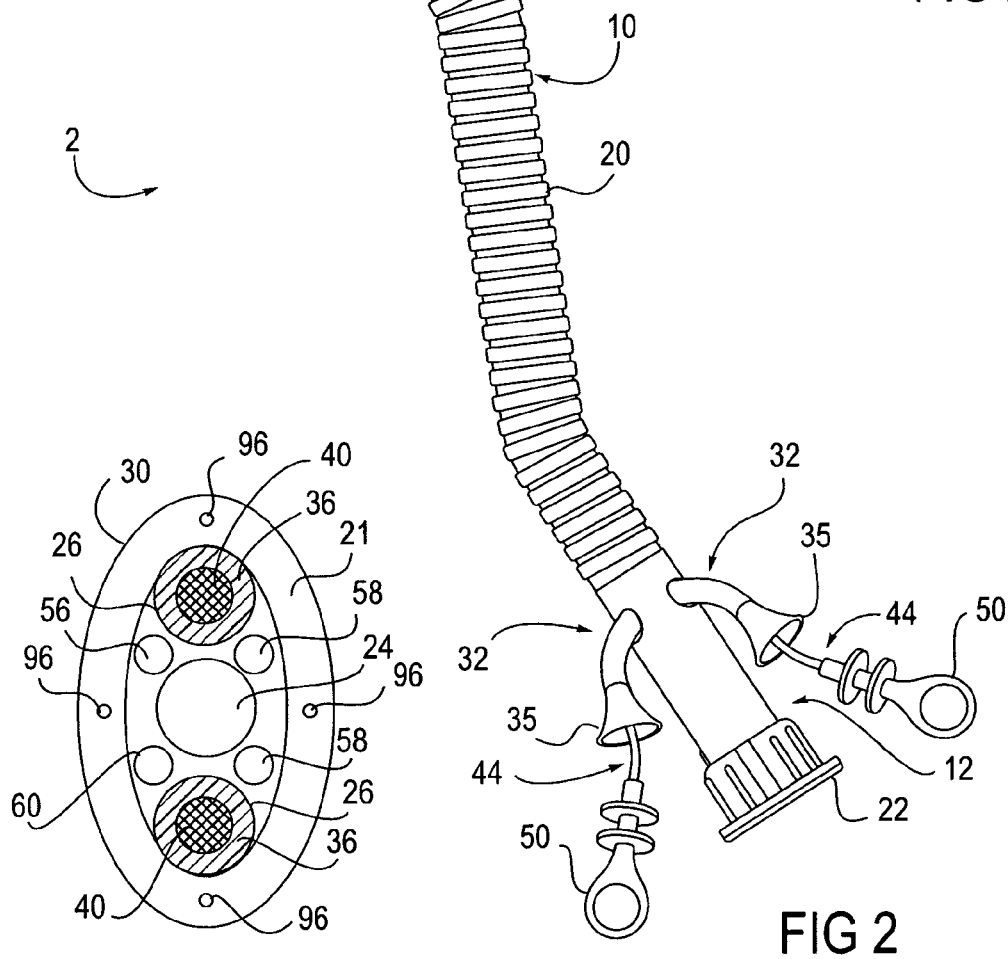
FIG 2A
FIG 2B
FIG 2

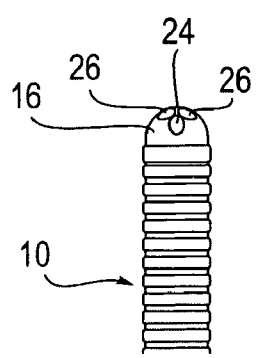
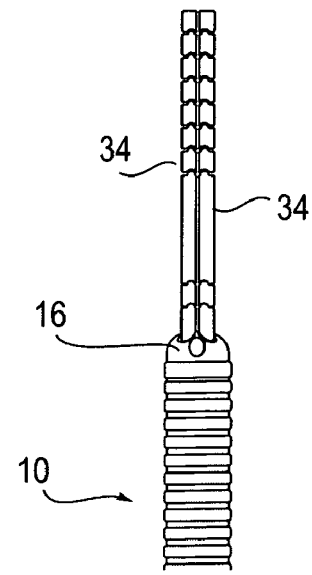
FIG 3A
FIG 3B
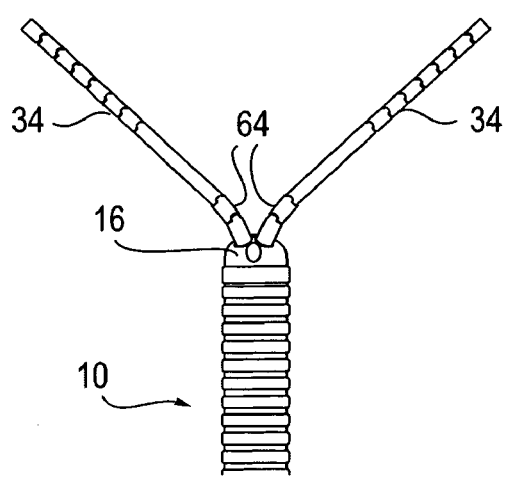
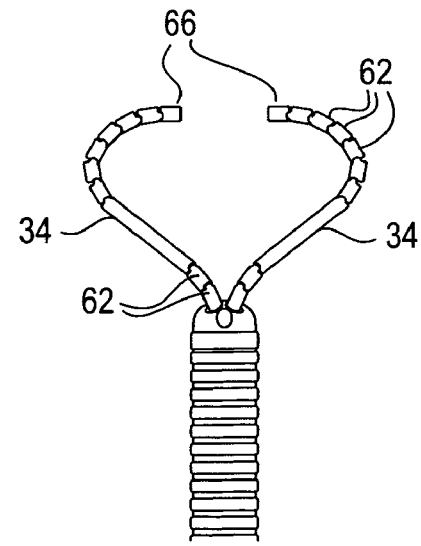
FIG 3C
FIG 3D

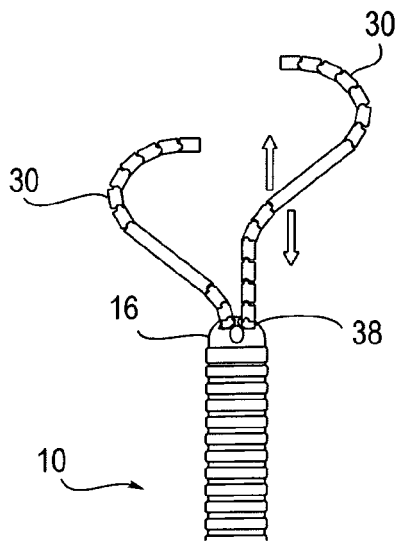 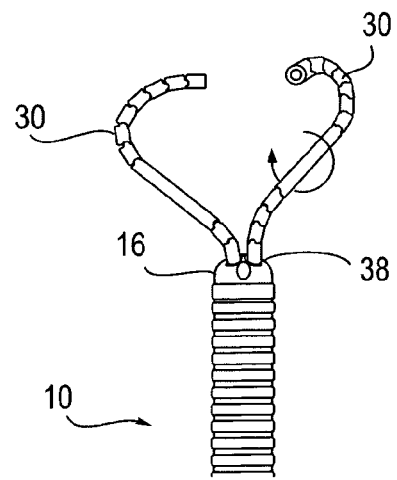
FIG 4  FIG 5
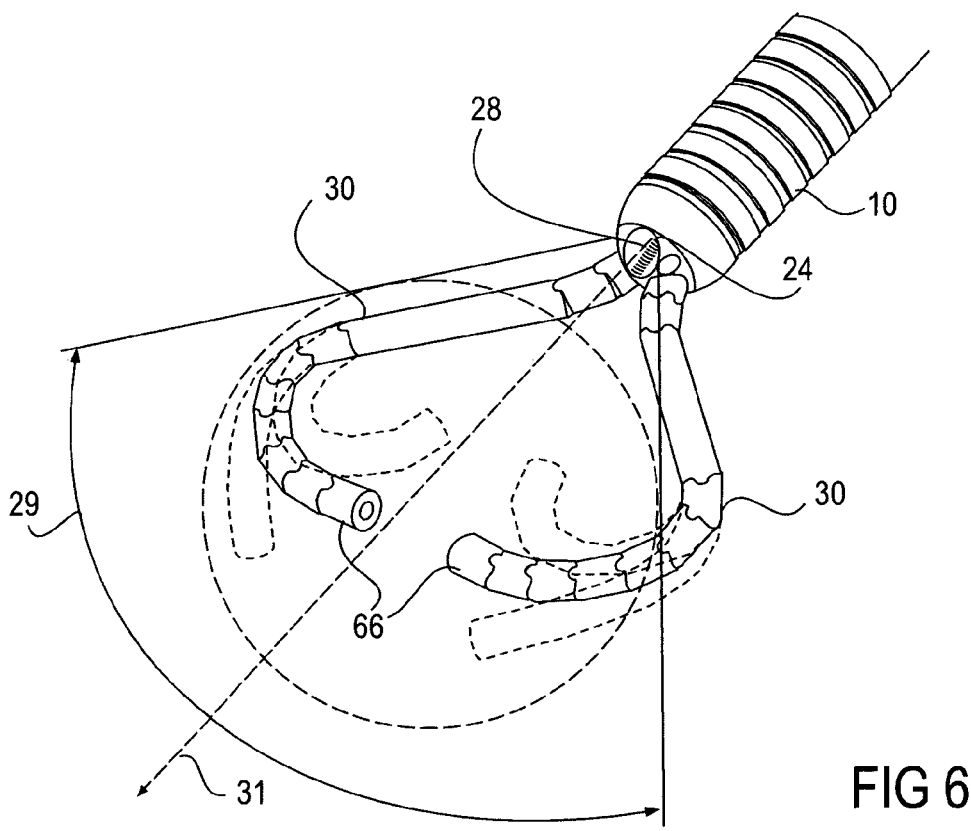
FIG 6

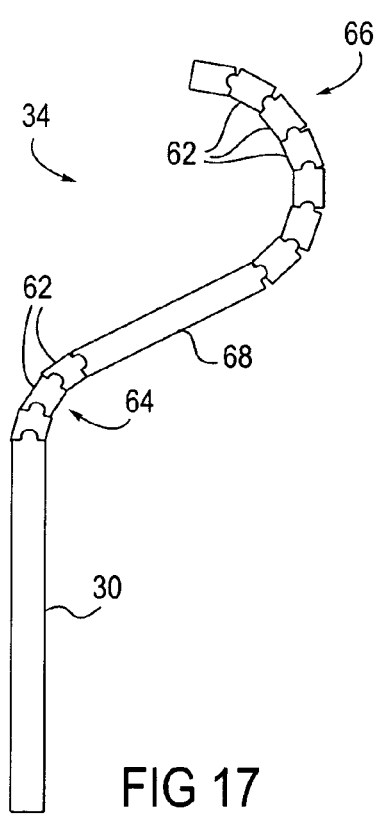
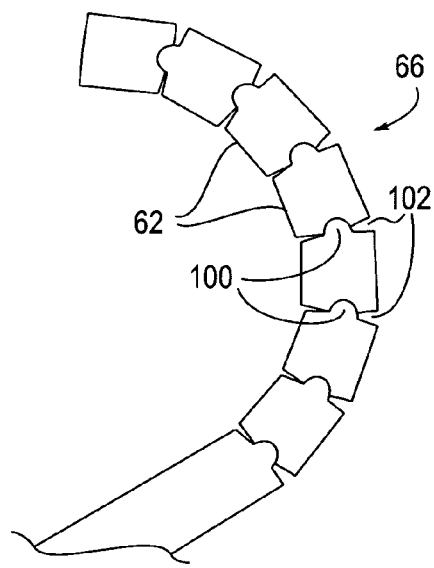
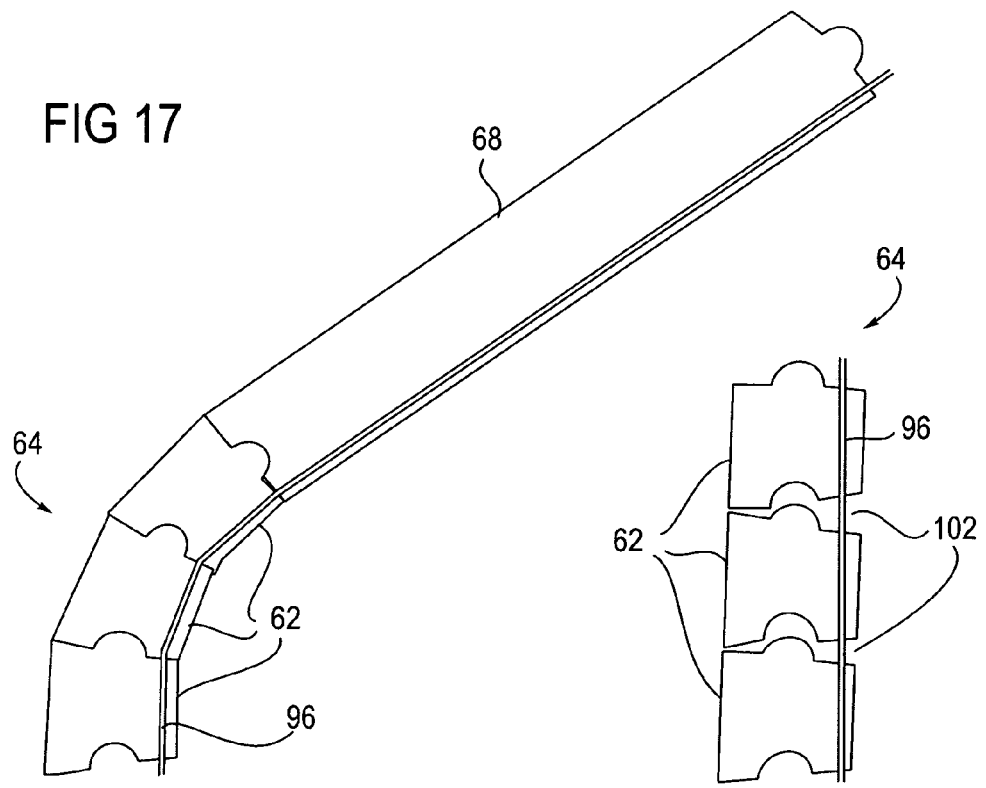
FIG 17
FIG 17A
FIG 17C
FIG 17B

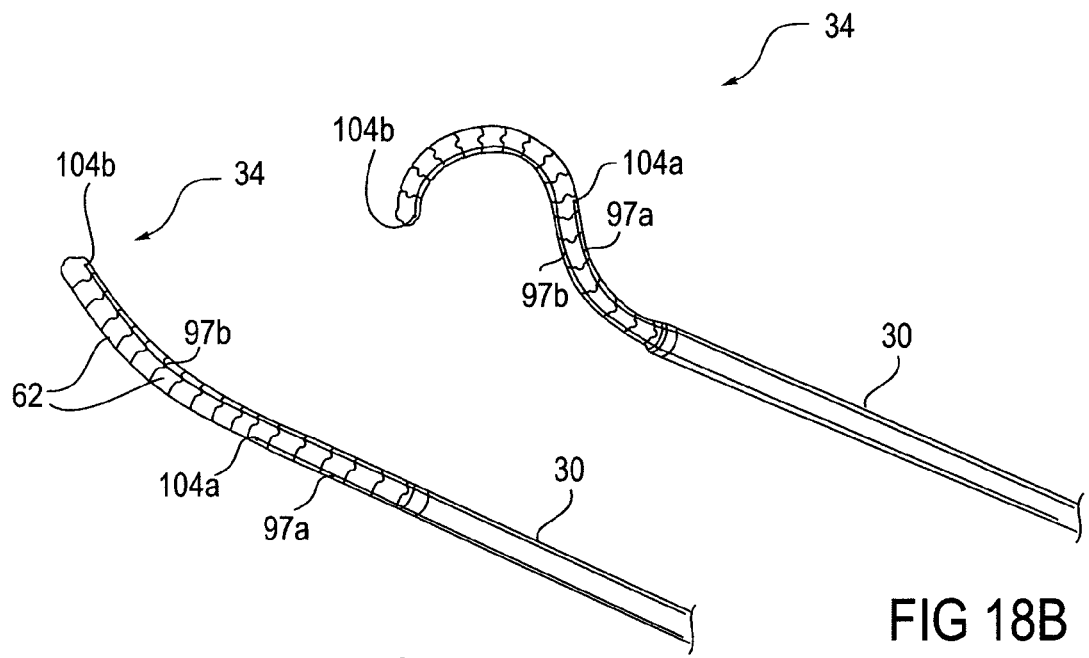
FIG 18B
FIG 18A
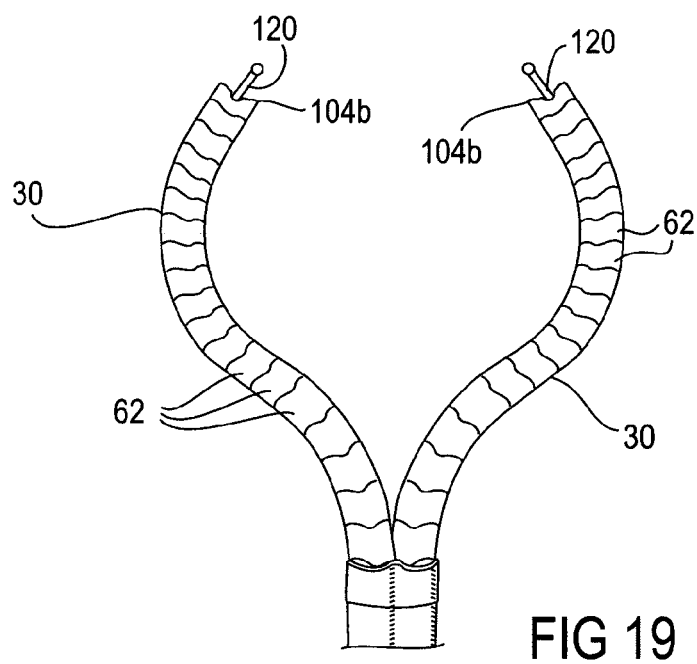
FIG 19

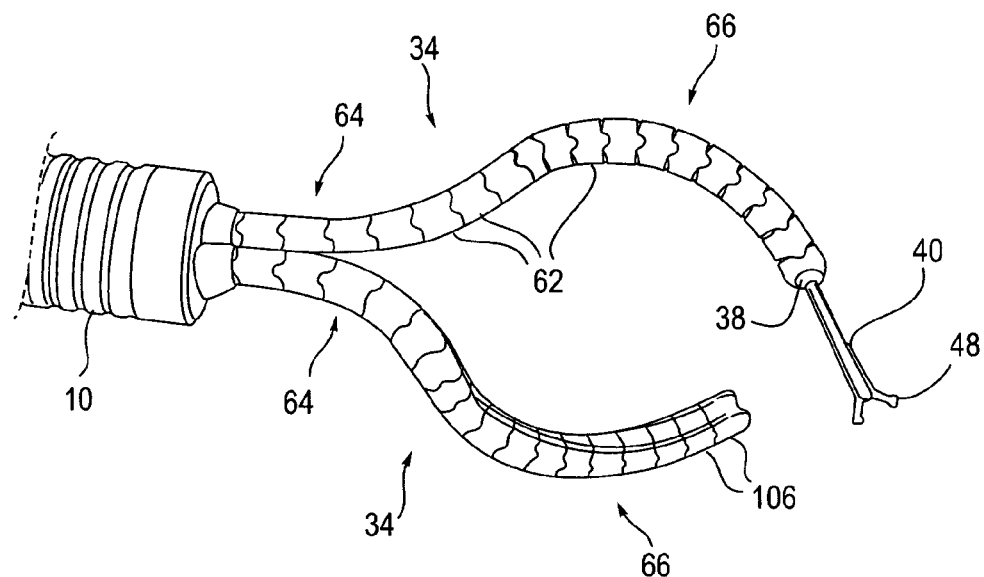
FIG 20
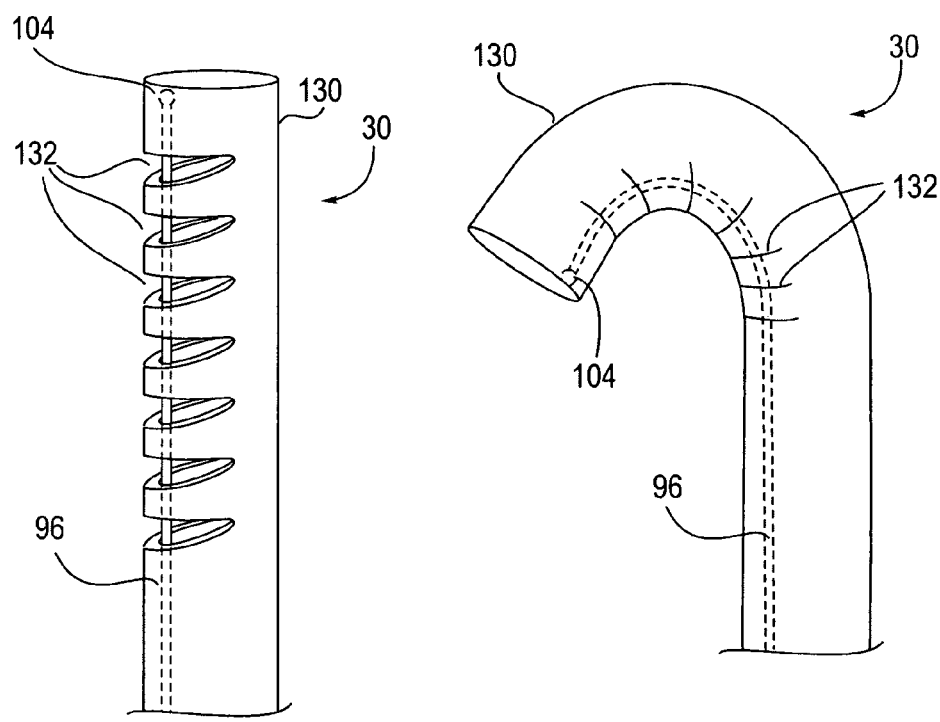
FIG 21A
FIG 21B

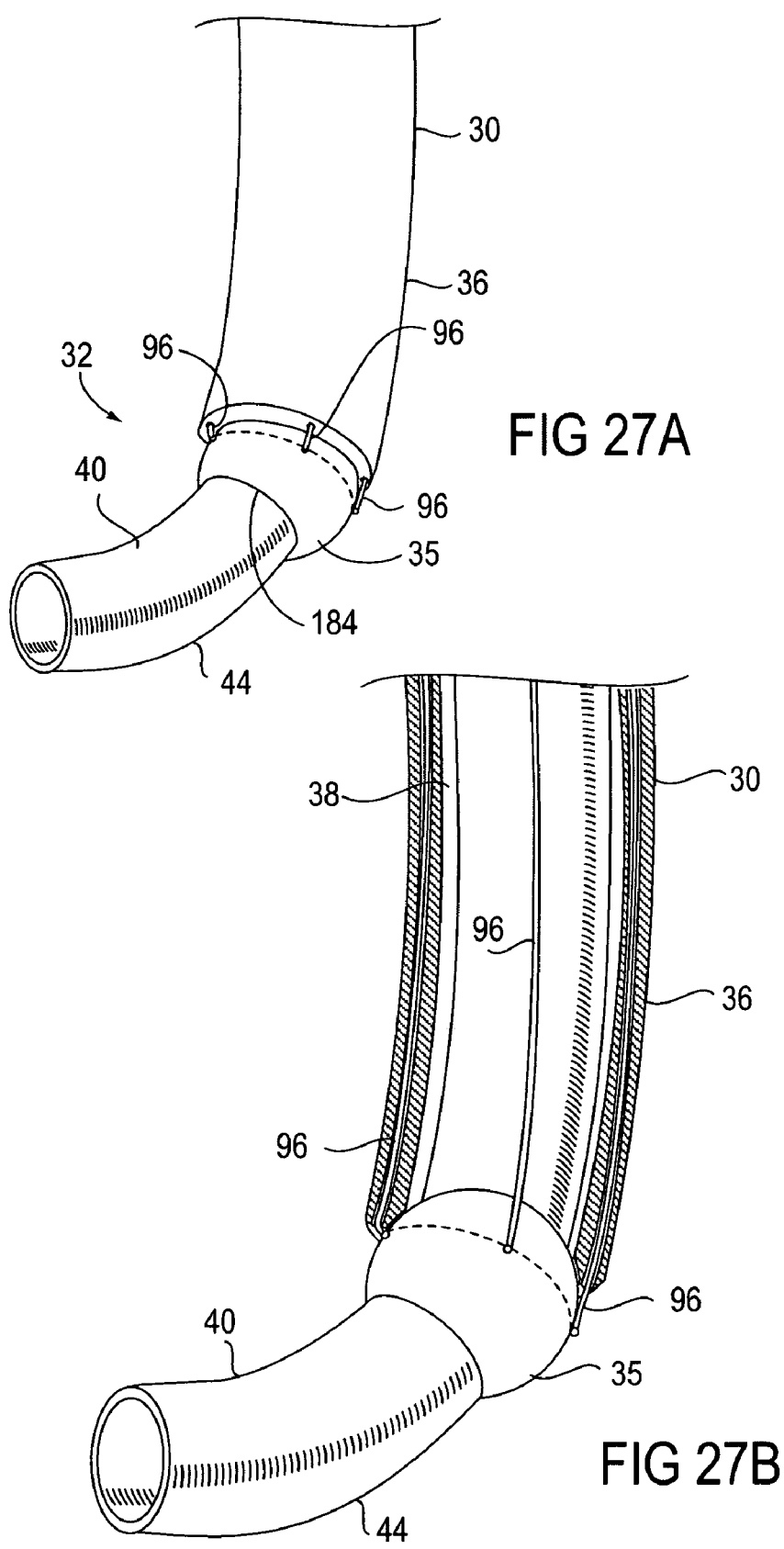

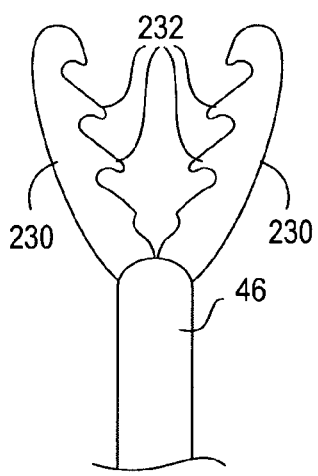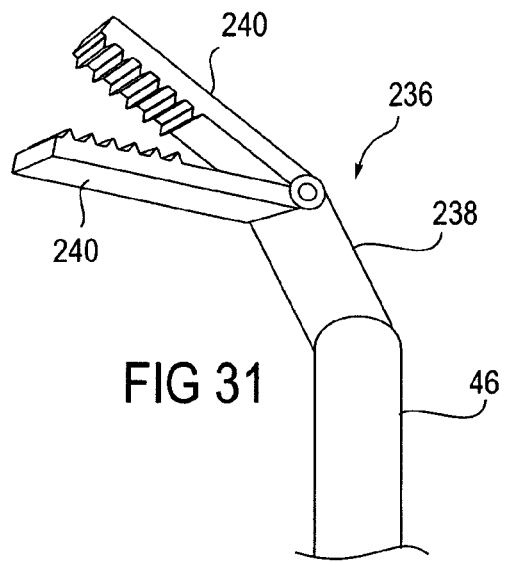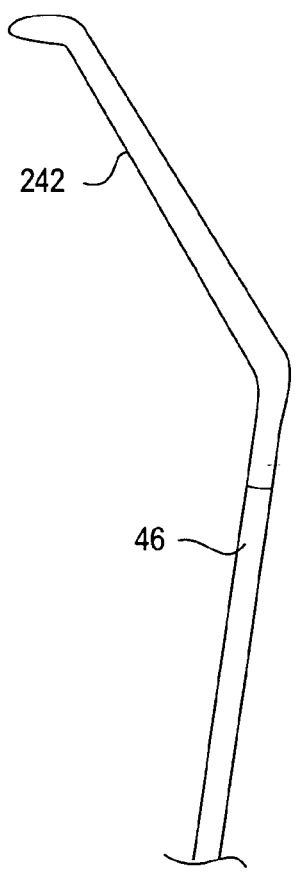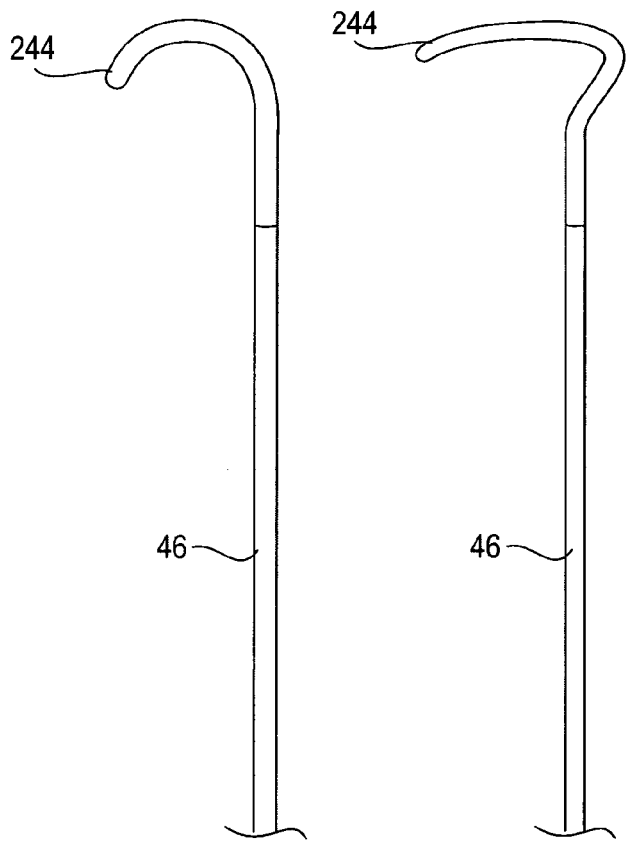
FIG 30
FIG 31
FIG 32
FIG 33
FIG 34

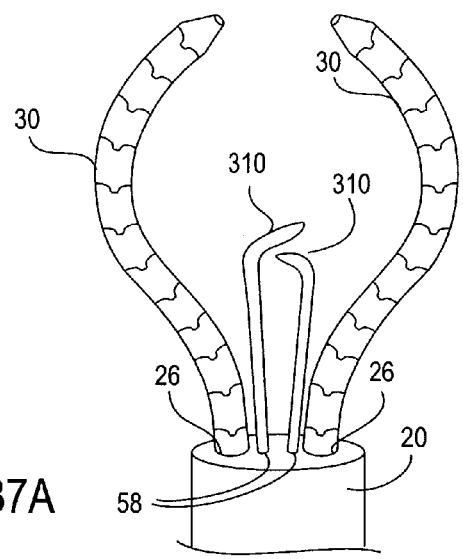
FIG 37A
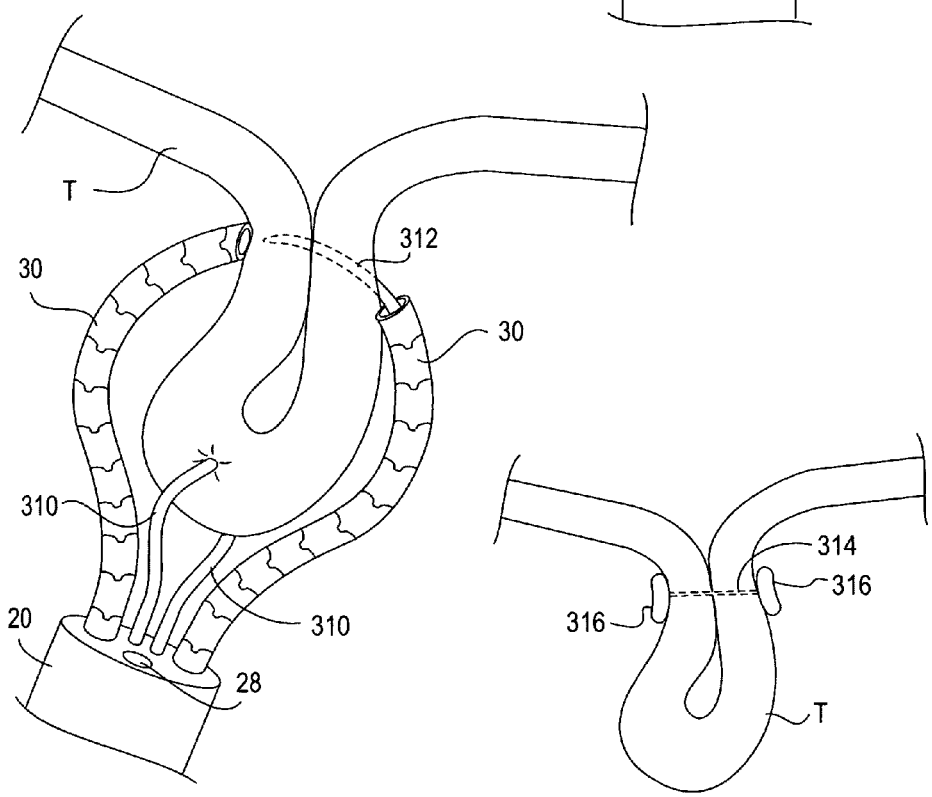
FIG 37B
FIG 37C

ENDOLUMINAL TOOL DEPLOYMENT SYSTEM

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

The present invention relates generally to medical devices, systems and methods. More particularly, the present invention relates to devices, systems and methods for use in endoscopic or laparoscopic procedures.

Endoscopy is a form of minimally invasive procedure wherein the interior of the body is accessed and visualized through an orifice in the body, such as the esophagus or rectum. Such access allows a surgeon or physician to view and/or treat internal portions of the orifice or internal tissues or organs which are accessible through the orifice. These procedures may be for diagnostic purposes, such as visual inspection or the removal of a tissue sample for biopsy, or the procedure may be used for treatment purposes, such as the removal of a polyp or tumor or the restructuring of tissue. While these procedures can be done using regular open surgery, endoscopy usually involves less pain, less risk, less scarring, and faster recovery of the patient.

Endoscopy is typically performed with the use of an endoscope, a small circular tube containing optical components. Traditional endoscopes comprise a small diameter "snake-like" insertion tube having a distal end which is inserted into the orifice to the desired internal location. Fiber optics extend through the insertion tube and terminate at the distal end to allow axial viewing from the distal end. Images of the internal location near the distal end of the endoscope are transmitted to a video monitor for the physician to view. A control handle allows the endoscopist to control the direction of the scope and in some cases, permits the actuation of air, water and suction utilities that may be required for the endoscopy procedure.

Since endoscopes may be used to perform a treatment at an internal location, some endoscopes are equipped with a lumen through which a surgical instrument or tool may be passed. Generally, the lumen extends through the length of the insertion tube to the distal end so that the end effector of the inserted instrument protrudes from the distal end in the axial direction. Thus, the instrument is directed in parallel to the fiber optics so that the end effector is positioned along the line of view.

Such endoscopes have a number of constraints which limit their usefulness in performing diagnostic and surgical procedures. To begin, surgical instruments and tools are inserted axially through a working lumen in the endoscope. And, most of these endoscopes only allow axial and rotational movement of the tool beyond the distal end. This helps to maintain positioning of the tool within the field of view of the endoscope which is also directed axially. However, this limits the variety and complexity of procedures that may be performed. For example, procedures which involve tissue approximation pose great difficulty since only one portion of tissue may be grasped at a time and lateral, rather than axial, movement may be required. Although steering of an axially inserted tool may be possible near the distal end, such steering typically positions the end effector of the tool out of the field of view of the axially directed scope.

A similar minimally invasive procedure which overcomes some of these constraints is laparoscopy. In laparoscopy, the interior of the body is accessed and visualized through a small incision. When accessing the abdomen, the incision is usually made in the navel. Laparoscopy was initially used by gynecologists to diagnose and treat conditions relating to the female reproductive organs: uterus, fallopian tubes, and ovaries. It is now used for a wider range of procedures, including operations that in the past required open surgery, such as removal of the appendix (appendectomy) and gallbladder removal (cholecystectomy). Laparoscopy is performed with a device which allows the surgeon or physician to view and/or treat internal tissues or organs which are accessible through the incision. This device is the same or similar to an endoscope, sometimes referred to as a laparoscope. The device comprises a small diameter insertion tube having a distal end which is inserted into the incision to the desired internal location. Fiber optics extend through the insertion tube and terminate at the distal end to allow axial viewing from the distal end. Images of the internal location near the distal end are transmitted to a video monitor for the physician to view. Sometimes, access through an incision creates a shorter, straighter and more direct access path than through an orifice. Therefore, some laparoscopes may have a shorter and stiffer insertion tube than some endoscopes.

Although laparoscopes suffer from many of the same limitations as endoscopes, laparoscopy allows additional surgical instruments and tools to be inserted through separate incisions to perform procedures. Proper location of the incisions can allow instruments to be positioned in various directions. Therefore, movement and viewing is not limited to the axis of the laparoscope and simultaneous viewing of the tissues and the instruments may be more readily achieved during the procedure. However, these additional benefits are achieved at the cost of increased invasiveness. Access paths must be created for the instruments with the use of trocars requiring general anesthesia, risk of complications and infection, and increased overall recovery time for the access paths to heal. In addition, access may be difficult or contraindicated in some patients, particularly in the morbidly obese.

Thus, it would be desired to provide an improved methods, devices and systems to perform minimally invasive procedures. Particularly, methods, devices and systems which would provide the benefits of endoscopy, such as lower invasiveness and access to deeply internal locations, with the benefits of laparoscopy, such as the use of multiple instruments with movement and viewing along various axes. The devices and systems would be reliable, convenient and easy to use with improved outcomes for patients due to reduction in invasiveness and therefore risk, cost and recovery time. At least some of these objectives will be met by the invention described hereinafter.

BRIEF SUMMARY OF THE INVENTION

The present invention provides systems, devices and methods for endoscopic procedures involving tissue manipulations beyond the capabilities of traditional endoscopic instruments. Embodiments of the systems include an elongated main body having a scope therethrough and at least one steerable tool arm which extends from the distal end of the main body. In preferred embodiments, the system includes two tool arms, each arm steerable to form a curve laterally outward which then bends laterally inward so that the arms form a an angular or boomerang shape. In addition, end effectors extend from the distal ends of each arm for use in manipulation of tissue. The angular shape brings the end effectors together in view of the scope for cooperative movements which are continuously visible by the surgeon through the scope. In addition, the tool arms may be steerable in any additional direction and may be rotateable to allow grasping, pulling, tugging, elevation and more complex manipulation of tissue. Thus, the systems and devices of the present invention provide many of the capabilities of open surgery or laparoscopic surgery with an endoscopic approach.

In a first aspect of the present invention, the tool arm(s) comprise a shaft having a proximal end and a deflectable or steerable distal end. In some embodiments, the steerable distal end will be laterally stabilized so that the distal end may be steered, i.e. bent or manipulated, within a plane but will resist deflection outside of the plane during use. The steering plane will generally be parallel to a central axis of the scope but may be rotated by rotation of the tool arm. In this way, the arm(s) will maintain stable positioning within the field of view of the scope and will resist accidental deflection outside of the field. It may be appreciated that the tool arm may also be translated axially within the stabilized plane while maintaining viewing within the field.

A preferred structure for achieving lateral stability comprises a plurality of adjacent links. Usually, the links are pivotally attached by hinged structures. In some embodiments, the hinged structures comprise pivot pins which are disposed parallel to one another and generally transverse to the stabilized plane in which the arm may be steered. In other embodiments, the hinged structures comprise male and female bearing surfaces which define axes, wherein the axes are disposed in parallel to limit deflection of the distal section to within the plane. A variety of other structures are also available to provide lateral stability, such as deployment frames, various shaped linkages connected by reinforcements or pullwires, and slotted tubes, to name a few.

Typically, the distal end includes at least two steerable sections, wherein a distal-most steerable section includes a tip section which curves in a first direction and wherein an intermediate steerable section includes a base which curves in the opposite direction, where both curves are in the stabilized plane. In some embodiments, the tip section curve has a radius which is greater than that of the curve of the base. To achieved such curvatures, the adjacent links may be shaped to allow substantially continuous deflection. Or, the adjacent links may be shaped so that the steerable distal end is deflectable to form a predetermined curvature wherein the arm is then restricted from further deflection.

Means for selectively deflecting the distal section of the tool arm(s) often comprise at least one pullwire or one pushwire. Such pull or pushwires may be present in any quantity and arrangement. The means for selectively deflecting the distal section can further include at least one spring which is configured to straighten the distal section in opposition to the pullwire or pushwire.

In some embodiments, the tool arm includes an end effector disposed at its distal end. A wide variety of end effectors may be used depending on the procedure or tissue manipulations which are desired. For example, end effectors may include but are not limited to knives, needles, sutures, staplers, fasteners, clippers, electrosurgical or hemostatic cutters and coagulators, laser welders, cryosurgery instruments, secondary scopes, forceps, lasers hooks, tongs, graspers, retractors, probes, clamps, scissors, tissue approximation devices and suction applicators. Alternatively, the tool arm may include a tool deployment lumen through which a tool having an end effector may be passed. In these embodiments, the tool arm may include a steering cuff arranged for passage of the tool therethrough so that manipulation of the tool within the steering cuff steers the distal end of the tool arm. Thus, in either case, manipulation of the end effector and the tool arm may be interconnected.

In another aspect of the present invention, the elongated main body has a distal end, a proximal end, and an arm guide lumen extending through at least a distal section of the elongated main body. In preferred embodiments, the elongated main body has a viewing scope lumen extending therethrough and terminating in the distal tip. The arm guide lumens and the viewing scope lumen may be arranged in any suitable fashion within the main body. For example, when the elongated main body has a second arm guide lumen, the distal terminations of the two arm guide lumens and the one viewing scope lumen may be arranged in a generally triangular pattern on the distal tip of the main body. Alternatively, the lumens may be aligned, wherein the viewing scope lumen is disposed between the arm guide lumens.

Typically, at least the distal section of the elongated main body is steerable. In some embodiments, the elongated main body comprises a first section and a second section disposed proximally of the first section, and the first and second sections are independently lockable. Thus, the first section may be lockable while the second section remains steerable. Such steering may be achieved with means for selectively deflecting the second section within at least a single plane. This may include retroflexion wherein the distal end of the main body is directed toward the proximal end. In some embodiments, the distal section of the elongated main body comprises a plurality of adjacent links to allow for such steering.

Typically, at least the distal section of the elongated main body has a generally cylindrical exterior wherein the arm guide lumen does not extend out of the cylindrical exterior. And, the arm guide lumen terminates at a distal tip of the elongated main body so that the tool arm advances through the distal tip. Likewise, as mentioned previously, the elongated main body typically has a viewing scope lumen extending therethrough and terminating in the distal tip.

In yet another aspect of the present invention, the tool arms may have a distal end which is steerable by a variety of mechanisms. For example, the distal end may be comprised of a flexible tube having at least one pullwire attached thereto so that manipulation of the at least one pullwire deflects the steerable distal end. Or, the tool arm may have a steerable distal end which comprises a flexible tube having shape memory material so that emergence of the steerable distal end from the distal tip of the main body allows deflection of the steerable distal end to a shape memory position. Or, the tool arm may further comprise a deployment frame extending from the distal tip of the main body, the frame comprising at least two supports each attached to one of the at least two tool arms so that manipulation of the deployment frame deflects the attached tool arms.

In an additional embodiment of the present invention, the endoluminal tool deployment system may be comprised of an elongated main body having a distal end, a proximal end, and at least two arm guide lumens extending over or through at least a distal section of the elongated main body, wherein said arm guide lumens extend fully to a distal tip of the main body, and at least two tool arms adapted to extend through the arm guide lumens of the elongated main body, said tool arms emerging from the distal tip of the main body.

In still another aspect of the present invention, the endoluminal tool deployment system comprises an elongated main body having a distal end, a proximal end, and an arm guide lumen extending through at least a distal section of the elongated main body, wherein at least the distal section comprises a plurality of adjacent links. The system further includes a means for selectively deflecting the distal section within at least a single plane, and at least one tool arm adapted to extend through the arm guide lumen of the elongated main body.

In a further aspect of the present invention, a method is provided for deploying one or more tools in an anatomical space. In a preferred embodiment, the method comprises introducing a distal end of a main body to said anatomical space, advancing a tool arm from a tool deployment lumen in said main body into said anatomical space, deflecting and positioning the tool arm to locate a distal tip thereof adjacent to a target location within the anatomical space, wherein a distal section of the arm is curved and laterally stabilized in a single plane, and advancing a tool through a lumen of the tool arm to the target location.

In some embodiments, deflecting and position comprises tensioning a plurality of adjacent hinged links within the distal section of the tool arm. The adjacent hinged links may be joined by hinge pins which are disposed perpendicularly to the single plane such that the pins stabilize the distal section and inhibit deflection outside of the single plane. The method may further comprise viewing the target location through a viewing scope disposed in the main body, wherein the tool arm extends axially from a distal tip of the main body from a location adjacent to the viewing scope.

Other objects and advantages of the present invention will become apparent from the detailed description to follow, together with the accompanying drawings.

BRIEF DESCRIPTION OF THE DRAWINGS

FIG. 2 illustrates the system of FIG. 1 in an assembled arrangement.

FIG. 2A depicts the cross-section of the system of FIG. 2, and FIG. 2B depicts an alternative cross-section.

FIGS. 3A-3D, 4-6 illustrate possible movements of the steerable distal ends of the tool arms.

FIGS. 17, 17A-17C illustrate an embodiment of a tool arm which is steerable to a predetermined arrangement.

FIGS. 18A-18B illustrate the creation of distinct curvatures achieved by separate pullwires.

FIG. 19 illustrates two tool arms steered to a predetermined arrangement.

FIG. 20 illustrates an embodiment including both links which are steerable to a predetermined arrangement and links which are unrestrictedly steerable.

FIGS. 21A-21B illustrate an embodiment of a tool arm comprised of a slotted tube.

FIGS. 26, 27A-27B, 28A-28B illustrate embodiments of a steering cuff.

FIG. 30 illustrates an embodiment of the tool having an end effector in the form of gator toothed graspers.

FIG. 31 illustrates an embodiment of the tool having an end effector in the form of an articulatable grasper.

FIGS. 32-36 illustrate embodiments of the tool having end effectors in the form of various shaped retractors.

FIGS. 37A-37B illustrate grasping hooks inserted through auxiliary lumens in the main body and FIG. 37C illustrates a fixation device which may be deployed by the tool arms when such grasping hooks are used in a plication procedure.

DETAILED DESCRIPTION OF THE INVENTION

I. Overview

Figure 1:
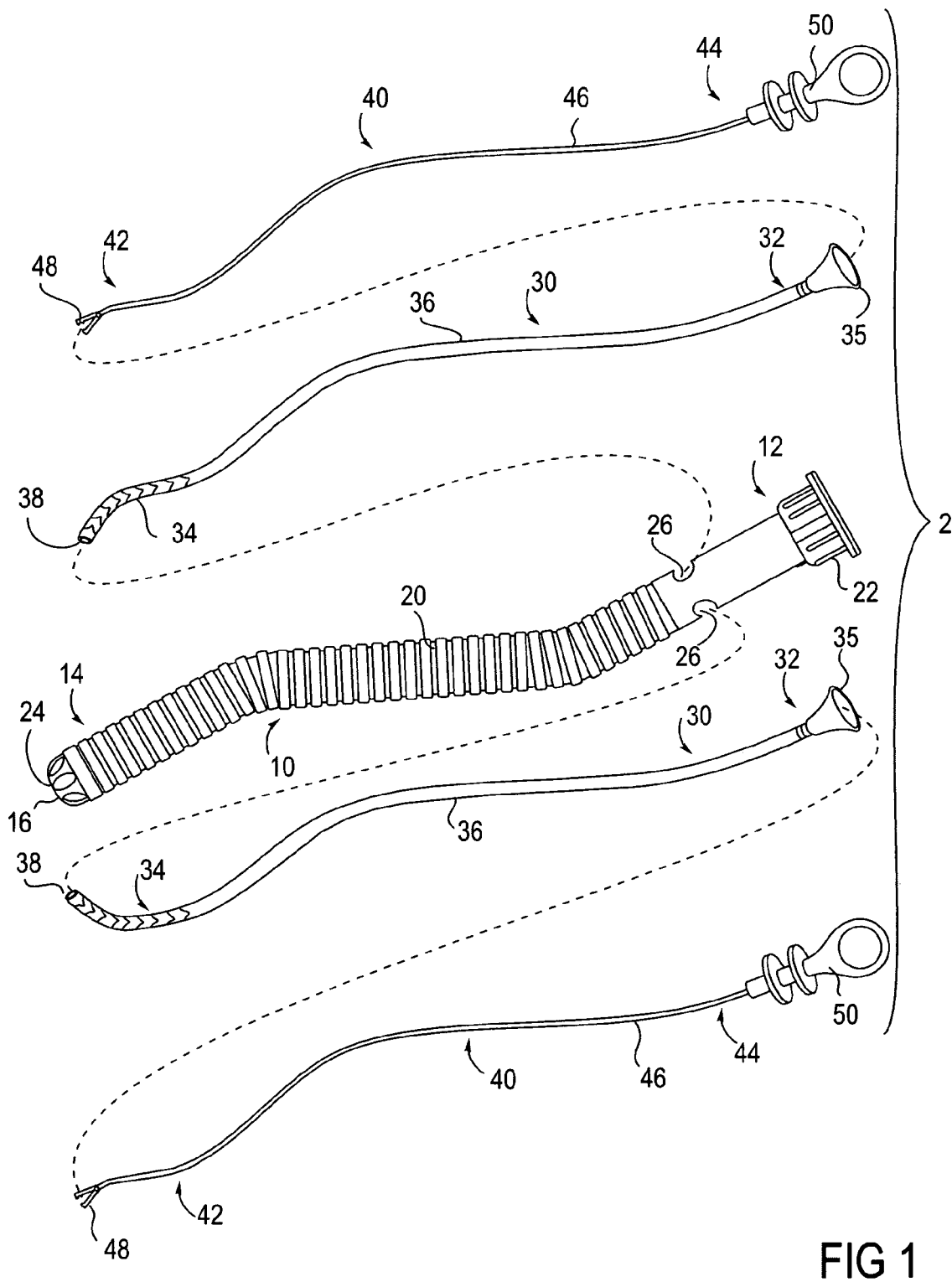
FIG. 1 illustrates an embodiment of a system of the present invention.

An embodiment of a system 2 of the present invention is illustrated in FIG. 1. The system 2 includes an elongated main body 10 having a proximal end 12 and a distal end 14 terminating in a distal tip 16. The main body 10 is used to access an internal target location within a patient's body. Typically, the distal end 14 is passed through a body orifice and one or more naturally occurring body lumens to the target location, such as in endoscopy, while the proximal end 12 remains outside of the body. Therefore, the main body 10 has a deflectable and/or steerable shaft 20, either due to choice of material or design of the shaft 20 to include links, hinges, coils or other similar structures to allow deflection. Thus, FIG. 1 illustrates the main body 10 in a deflected position wherein the body 10 includes curvatures. Such deflection and/or steering may be useful in traversing body lumens to the target location and is achievable by manipulation of a handle 22 near the proximal end 12. It may be appreciated, however, that the system 2 may be used in laparoscopic procedures wherein such deflection and/or steering may be less utilized for placement of the main body 10. In either case, rigidization of some or all the shaft 20 may be desired, for example to provide a stable visualization platform. Therefore, portions of the shaft 20 of the main body 10 are lockable to maintain a desired shape and provide rigidity, either due to choice of material or design of the shaft 20 to include locking mechanisms, as will be described in later sections.

The main body 10 also includes at least one arm guide lumen 26 which extends over or through at least a distal section of the main body 10, typically along the majority of the length of the body 10 as shown. Here in FIG. 1, two arm guide lumens 26 are shown, each extending from a position along the shaft 20 near the proximal end 12 to the distal tip 16. In addition, the main body 10 includes a scope lumen 24 which extends through the shaft 20 to the distal tip 16.

The system 2 also includes at least one tool arm 30, two are shown in FIG. 1, each arm 30 of which is insertable through a separate arm guide lumen 26 as indicated by dashed line. Each tool arm 30 has a proximal end 32, a distal end 34 and a shaft 36 therebetween. The distal end 34 is steerable, such as by manipulation of adjacent links as schematically indicated. Such steerability may be controlled by a steering cuff 35 which is part of the proximal end 32. The shaft 36 is typically flexible or deflectable to allow deflection of the surrounding main body shaft 20. Each tool arm 30 additionally includes a tool deployment lumen 38 therethrough.

In this embodiment, the system 2 also includes at least one tool 40, two are shown in FIG. 1. Each tool 40 includes a distal end 42, a proximal end 44 and an elongate shaft 46 therebetween to allow passage through the tool deployment lumen 38 of the arm 30. Each tool 40 has an end effector 48 disposed at the distal end 42 and optionally a handle 50 at the proximal end 44 for manipulation of the end effector 48 from outside the body. The tool 40 is advanced so that the end effector 48 emerges from the distal end 34 of the arm 30.

FIG. 2 illustrates the system 2 of FIG. 1 in an assembled arrangement. Here, the tool arms 30 are shown inserted through the arm guide lumens 26 of the main body shaft 20. The steerable distal ends 34 of the arms 30 protrude from the distal end 14 of the main body 10 and the proximal ends 32 of the arms 30 protrude from the proximal end 12 of the main body 10. As shown, the steering cuffs 35 are located at the proximal ends 32 of the arms 30. In addition, the tools 40 are shown inserted through the tool deployment lumens 38 so that the end effectors 48 extend beyond the steerable distal ends 34 of the arms 34. Likewise, the proximal ends 44 of the tools 40 with handles 50 are shown protruding from the steering cuffs 35. Movement of the tools 40 against the steering cuffs 35 will actuate steering of the distal ends 34 of the arms 30, as will be described in later sections.

FIG. 2A provides a cross-sectional view of system 2 of FIG. 2. Since the shaft 20 of the main body 10 has a generally cylindrical exterior in this embodiment, the cross-section of the shaft 20 has a circular shape. It may be appreciated that cylindrical shafts may alternatively have an elliptical, oval or oblong cross-section. The shaft 20 has an outer diameter in the range of about 5 to 25 mm, preferably approximately 14 mm. The shaft 20 has a wall 21 with a thickness in the range of about 0.5 to 5 mm, preferably about 2-3 mm, defining an inner central lumen 23. Within the wall 21 lies various push-wires or pullwires 96, hereinafter referred to as pullwires, for steering the main body 10 which may be present in a variety of quantities and arrangements. Alternatively, the pullwires 96 may be present within the central lumen 23. At least one arm guide lumen 26, two are shown, extend through the central lumen 23. Each arm guide lumen 26 has an inner diameter in the range of about 0.5 to 5 mm, preferably about 4 mm. Positioned within the lumens 26 are the shafts 36 of the tool arms 30. And, likewise, positioned within the shafts 36 are the tools 40. FIG. 2A also illustrates the scope lumen 24 which has an inner diameter in the range of about 2 to 10 mm, preferably about 4 mm. In this embodiment, the two arm guide lumens 26 and the scope lumen 24 are arranged in a generally triangular pattern which is maintained to the distal tip 16, however any suitable arrangement may be used which allows viewing of the tool arms, particularly the end effectors, by the scope. For example, FIG. 2B illustrates a cross-section of an embodiment wherein the shaft 20 has an oval shape and the arm guide lumens 26 and the scope lumen 24 are generally aligned. Here, the scope lumen 24 is disposed between the arm guide lumens 26 to facilitate viewing of the tool arms 30. Also illustrated in FIGS. 2A and 2B are additional lumens which may be used for various needs. For example, an irrigation/suction lumen 60, an insufflation lumen 56 and an auxiliary lumen 58 may be present, each having an inner diameter in the range of about 0.5 to 5 mm, preferably about 2 mm. The auxiliary lumen 58 may be utilized for a variety of uses, such as insertion of additional tools, such as a macerator, a grasping tool, a cutting tool or a light source, to name a few, for use in conjunction with the end effectors present at the distal ends of the arms 30 or the distal ends of the tools 40 inserted through the arms 30.

FIGS. 3A-3D illustrate a series of movements of the steerable distal ends 34 of the tool arms 30. This series serves only as an example, as a multitude of movements may be achieved by the distal ends 34 independently or together. FIG. 3A illustrates the distal tip 16 of the main body 10. The scope lumen 24 is shown along with two arm guide lumens 26 terminating at the distal tip 16 and forming a triangular pattern as illustrated in FIG. 2A. FIG. 3B illustrates the advancement of the distal ends 34 of the tool arms 30 through the arm guide lumens 26 so that the arms 30 extend beyond the distal tip 16. FIGS. 3C-3D illustrate deflection of the arms 30 to a preferred arrangement. FIG. 3C illustrates deflection of the arms 30 laterally outward. This is achieved by curvature in the outward direction near the base 64 of the steerable distal end 34. FIG. 3D illustrates deflection of the tip section 66 of the distal end 34 laterally inward achieved by curvature in the inward direction so that each arm 30 forms a hook shape. By facing the tip sections 66 of the arms 30 toward each other as shown, the tip sections 66 are positioned directly in the path of the scope lumen 24. Therefore, when a scope 28 is positioned within the scope lumen 24, the tip sections 66 of the tool arms 30 and any tools 40 advanced therethrough, will be visible through the scope 28. In FIGS. 3C-3D, deflection of the arms 30 is achieved with the use of adjacent links 62 in the areas of desired curvature. Embodiments of such links 62 and other mechanisms of deflection will be discussed in later sections. Further, the deflection of FIGS. 3A-3D are shown to be within a single plane. However, various embodiments include deflection in multiple planes. Likewise, the arms 30 are shown to be deflected simultaneously in FIGS. 3A-3D, however the arms 30 may be deflected selectively or independently.

FIGS. 4-6 illustrate additional possible movements of the tool arms 30. For example, FIG. 4 illustrates axial movement of the tool arms 30. Each tool arm 30 can independently move distally or proximally, such as by sliding within the tool deployment lumen 38, as indicated by arrows. Such movement maintains the arms 30 within the same plane yet allows more diversity of movement and therefore surgical manipulations. FIG. 5 illustrates rotational movement of the tool arms 30. Each tool arm 30 can independently rotate, such as by rotation of the arm 30 within the tool deployment lumen 38, as indicated by circular arrow. Such rotation moves the arm 30 through a variety of planes. By combining axial, lateral and rotational movement, the arms 30, and therefore the tools 40 positioned therethrough, may be manipulated through a wide variety of positions in one or more planes.

FIG. 6 illustrates further articulation of the tool arms 30. In some embodiments, the arms 30 are deflectable to form a predetermined arrangement, such as illustrated in FIG. 3D. Typically, when forming the predetermined arrangement, the arms 30 are steerable up until the formation of the predetermined arrangement wherein the arms 30 are then restricted from further deflection. In other embodiments, the arms are deflectable to a variety of positions and are not limited by a predetermined arrangement. Such an embodiment is illustrated in FIG. 6 wherein the arms 30 articulate so that the tip sections 66 curl inwardly toward the distal tip 16 of the main body 10. Again, the tip sections 66 are positioned in front of the scope lumen 24 and scope 28 for viewing. Typically, the tip sections 66 are positioned on opposite sides of a central axis 31 of the scope 28, wherein the field of view (indicated by arrow 29) spans up to approximately 140 degrees, approximately 70 degrees on each side of the central axis 31. In addition, the depth of field is typically in the range of approximately 1-10 cm.

Figure 7A:
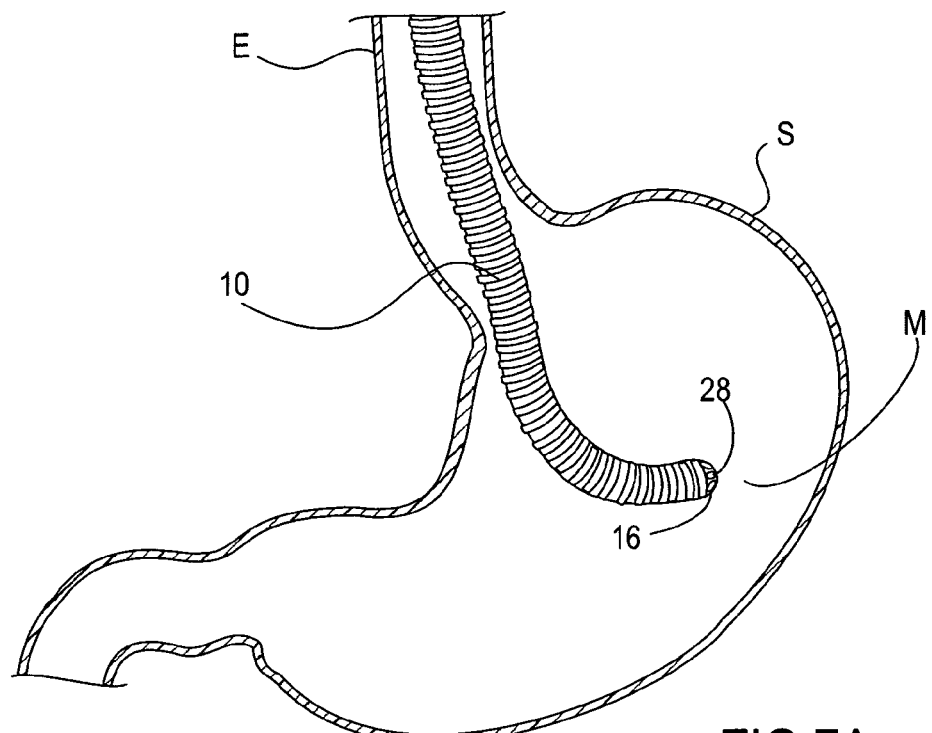
FIGS. 7A-7B illustrate the use of an embodiment of the system to perform a mucosectomy.
Figure 7B:
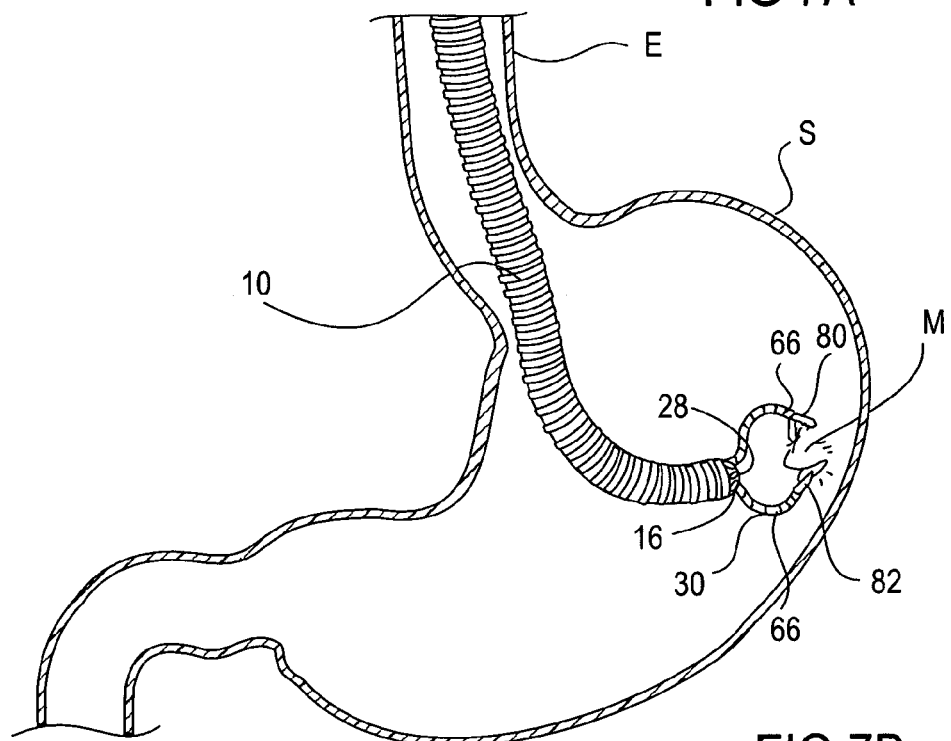

As mentioned previously, the endoluminal tool deployment system 2 of the present invention may be used to access a various internal tissues or organs to perform a wide variety of surgical procedures. FIGS. 7A-7B illustrate the use of an embodiment of the system 2 to perform a mucosectomy, or removal of a portion of the mucosa and/or submucosa of the stomach. FIG. 7A illustrates advancement of the main body 10 through the esophagus E to the stomach S. The main body 10 is then steered to a desired position within the stomach S and the stomach mucosa M is visualized through the scope 28 at the distal tip 16. Referring to FIG. 7B, the tool arms 30 are then advanced through the main body 10 and articulated. As mentioned, tools 40 may be advanced through the tool arms 30 or an end effector 48 may be disposed at the distal end of each arm 30. Here, a grasper 80 is disposed at the distal end of one arm 30 and a cutter 81 is disposed at the distal end of the other arm 30. The grasper 80 is used to grasp a portion of the mucosa M. The grasped portion of mucosa M can then be elevated by rotation or manipulation of the tool arm 30. This allows safe resection of the portion of mucosa M by cutting with the use of the cutter 82, as shown. Manipulation and resection of the tissue is visualized throughout the procedure through the scope 28 which is aligned with the tip sections 66, and therefore end effectors 48.

It may be appreciated that the systems, methods and devices of the present invention are applicable to diagnostic and surgical procedures in any location within a body, particularly any natural or artificially created body cavity. Such locations may be disposed within the gastrointestinal tract, urology tract, peritoneal cavity, cardiovascular system, respiratory system, trachea, sinus cavity, female reproductive system and spinal canal, to name a few. Access to these locations may be achieved through any body lumen or through solid tissue. For example, the stomach may be accessed through an esophageal approach, the heart through a port access approach, the rectum through a rectal approach, the uterus through a vaginal approach, the spinal column through a port access approach and the abdomen through a port access approach.

A variety of procedures may be performed with the systems and devices of the present invention. The following procedures are intended to provide suggestions for use and are by no means considered to limit such usage: Laryngoscopy, Rhinoscopy, Pharyngoscopy, Bronchoscopy, Sigmoidoscopy (examination of the sigmoid colon, the sigmoid colon is the portion that connects the descending colon to the rectum; primarily for diagnostic purposes, however a biopsy procedure and trans anal micro surgery may be performed for removing tumors), Colonoscopy (examination of colon; for the removal of polyps and tumors or for biopsy), and Esophagogastroduodenoscopy (EGD) which enables the physician to look inside the esophagus, stomach, and duodenum (first part of the small intestine). The procedure might be used to discover the reason for swallowing difficulties, nausea, vomiting, reflux, bleeding, indigestion, abdominal pain, or chest pain.

In addition, endoscopic retrograde cholangiopancreatography (ERCP) may be achieved which enables the surgeon to diagnose disease in the liver, gallbladder, bile ducts, and pancreas. In combination with this process endoscopic sphincterotomy can be done for facilitating ductal stone removal. ERCP may be important for identification of abnormalities in the pancreatic and biliary ductal system. Other treatments include Cholecystectomy (removal of diseased gallbladder), CBD exploration (for common bile duct stones), appendicectomy (removal of diseased appendix), hernia repair TAP, TEPP and other (all kinds of hernia), fundoplication and HISS procedures (for gastro esophageal reflux disease), repair of duodenal perforation, gastrostomy for palliative management of late stage upper G.I.T. carcinoma), selective vagotomy (for peptic ulcer disease), splenectomy (removal of diseased spleen), gastric restrictive and malabsorbtive procedures (for morbid obesity), upper and lower G.I. endoscopies (diagnostic as well as therapeutic endoscopies), pyloroplastic procedures (for children's congenital deformities), colostomy, colectomy, adrenalectomy (removal of adrenal gland for pheochromocytoma), liver biopsy, gastrojejunostomy, subtotal liver resection, gastrectomy, small intestine partial resections (for infarction or stenosis or obstruction), adhesions removal, treatment of rectum prolaps, Heller's Myotomy, devascularization in portal hypertension, attaching a device to a tissue wall and local drug delivery to name a few.

II. Main Body

Figure 8A:
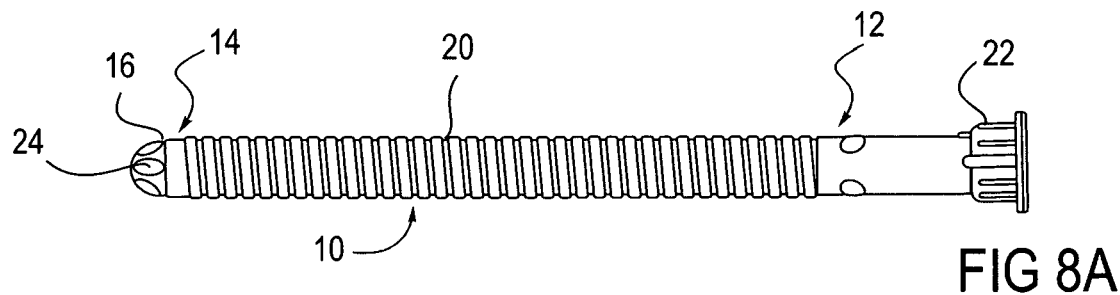
FIGS. 8A-8C illustrate an embodiment of the main body in a variety of positions.
Figure 8B:
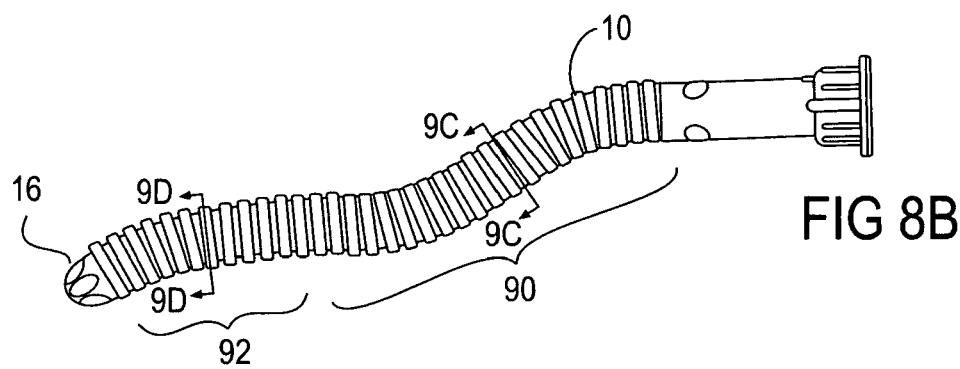
Figure 8C:
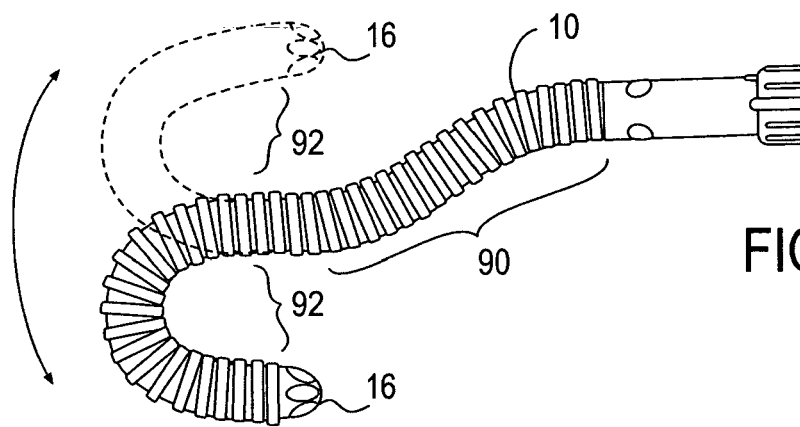

As mentioned previously, the system 2 of the present invention includes an elongated main body 10 having a proximal end 12 and a distal end 14 terminating in a distal tip 16. An embodiment of the main body 10 is illustrated in FIG. 8A in a straight configuration. However the main body 10 is used to access an internal target location within a patient's body so the main body 10 has a deflectable and/or steerable shaft 20. Thus, FIG. 8B illustrates the main body 10 having various curvatures in its deflected or steered state. In preferred embodiments, the main body 10 is steerable so that the main body 10 may be advanced through unsupported anatomy and directed to desired locations within hollow body cavities. In some embodiments, the main body 10 includes a first section 90 which is proximal to a second section 92, as indicated in FIG. 8B. Although both sections 90, 92 are steerable, the first section 90 may be locked in place while the second section 92 is further articulated. This is illustrated in FIG. 8C, wherein the first section 90 is shown in a locked position unchanged from FIG. 8B and the second section 92 is shown in various retroflexed positions. In retroflexion, the second section 92 is curved or curled laterally outwardly so that the distal tip 16 is directed toward the proximal end 12 of the main body 10. Optionally, the second section 92 may also be locked, either in retroflexion or in any other position.

Figure 9A:
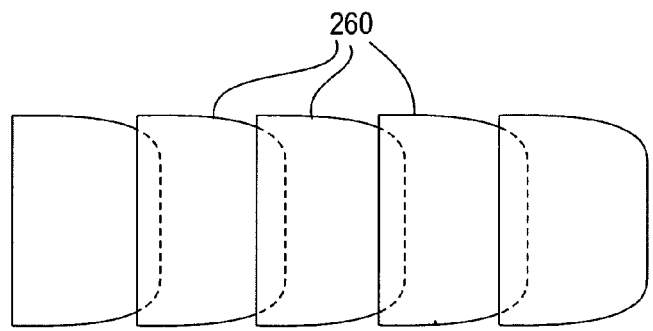
FIG. 9A shows an embodiment of the shaft of the main body comprised of a multiplicity of nestable elements, and FIG. 9B provides an exploded view of these elements.
Figure 9B:
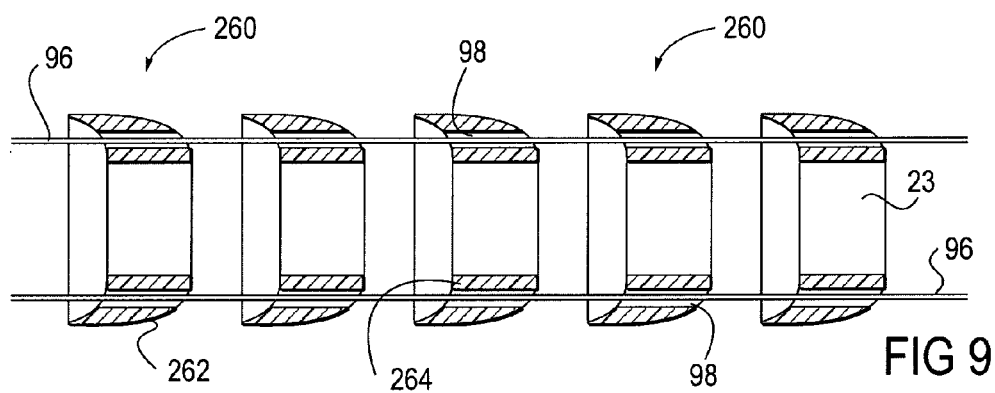
FIGS. 9C-9E provide cross-sectional views of various nestable elements.

Steering and locking may be achieved by any suitable mechanisms. In some embodiments, the shaft 20 comprises a multiplicity of nestable-elements 260, as illustrated in FIG. 9A. FIG. 9B provides an exploded view of the nestable elements 260 of FIG. 9A. Here it can be seen that the elements 260 are disposed so that a distal surface 262 of one element 260 coacts with a proximal surface 264 of an adjacent element. Each of the nestable elements 260 includes one or more pullwire lumens 98 through which pullwires 96 pass. The pullwires 96 are used to hold the elements 260 in nesting alignment and to provide steering and locking. The pullwires 96 preferably are made from a superelastic material, e.g. nickel titanium alloy, to provide flexibility, kink-resistance and smooth movement of the pullwires 96 through the pullwire lumens 98. Alternatively, the pullwires 96 may be made from braided stainless steel, a single stainless steel wire, poly-para-phenylene terephthalamide (such as Kevlar®), a high tensile strength monofilament thread, combinations thereof or any suitable materials.

Figure 9C:
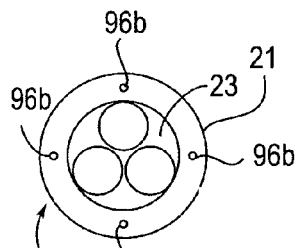

Generally, the adjacent surfaces 262, 264 are contoured to mate so that when the pullwires 96 are relaxed, surfaces 262, 264 can rotate relative to one another. This allows the shaft 20 to form curvatures throughout its length in any direction. Each pullwire 96 is fixed at its distal end to a specific element 260 along the shaft 20 or to the distal tip 16. When tension is applied to a specific pullwire 96, a curvature forms in the shaft 20 proximal to the fixation point, thus steering the shaft 20. The pullwires 96 may be arranged in various patterns to achieve steering in various directions. For example, FIG. 9C is a cross-sectional view of the shaft 20 in the first section 90 of FIG. 8B. Here, eight pullwires 96 (four pullwires 96a and four pullwires 96b) are shown passing through the wall 21. Four pullwires 96a terminate at the distal end of the first section 90 and are used to steer the first section 90. Since the pullwires 96a are equidistantly positioned, applying tension to the pullwires 96a, either individually or in combination, steers the first section 90 in any desired direction. The first section 90 may be locked in place by holding the tension in the pullwires 96a using any suitable mechanisms. For example, tension may be applied to the pullwires 96 simultaneously until the elements 260 are compressed to a state in which they are locked by friction wherein the tension is held.

Figure 9D:
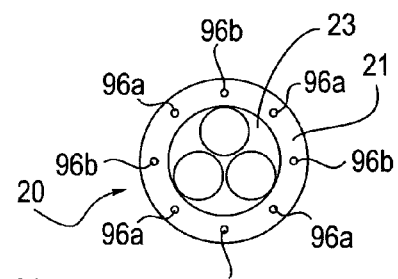

FIG. 9D is a cross-sectional view of the shaft 20 in the second section 92 of FIG. 8B. Here, four pullwires 96b are shown passing through the wall 21. These pullwires 96b extended through the first section 90, as indicated in FIG. 9C, and terminate near the distal tip 16. Since the pullwires 96b are equidistantly positioned, applying tension to the pullwires 96b, either individually or in combination, steers the second section 92 in any desired direction. Since the pullwires 96b also pass through the first section 90, such steering may also effect the curvature in the first section 90 when the first section is not locked. However, such effects are minimal, may be counteracted or compensated for by steering in the first section 90, and may be avoided by locking. The second section 92 may be also be locked in place by holding the tension in the pullwires 96b using any suitable mechanisms.

In this embodiment, the wall 21 extends continuously from the proximal end 12 to the distal end 14 with the first and second sections 90, 92 determined by the termination points of the pullwires 96a which extend therethrough. Alternatively, the first and second sections 90, 92 may be comprised of separate shafts which are coaxially positioned adjacent to one another.

Figure 9E:
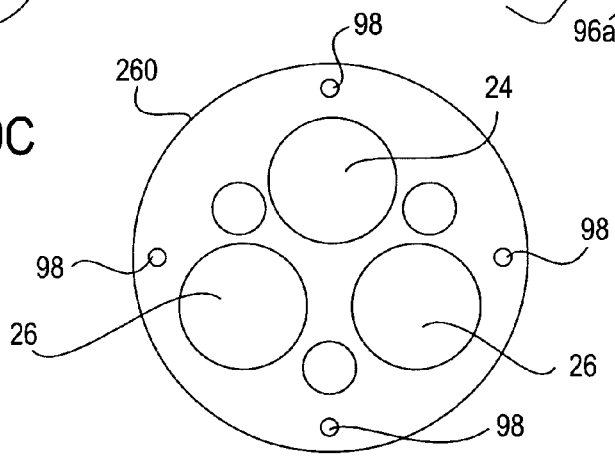
Figure 10A:
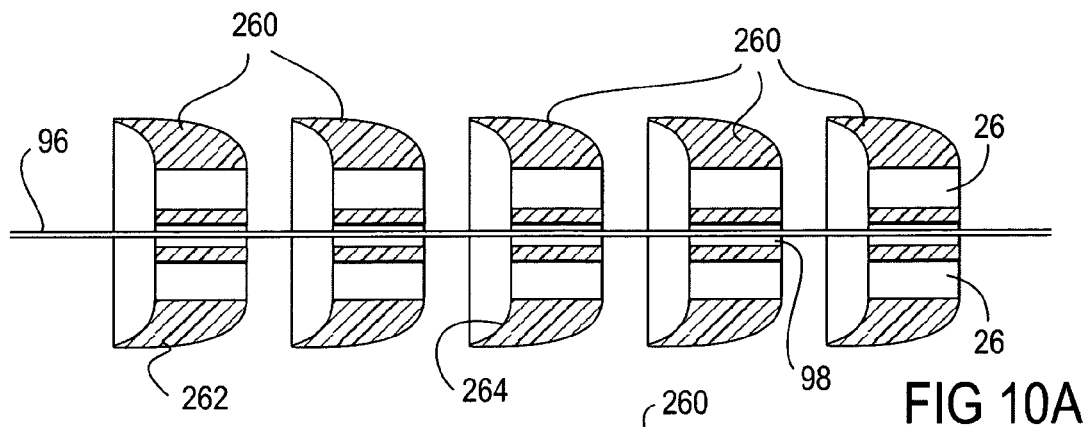
FIG. 10A provides an exploded view of nestable elements having a pullwire extending through their centers and FIG. 10B provides a cross-sectional view one of the nestable elements.
Figure 10B:
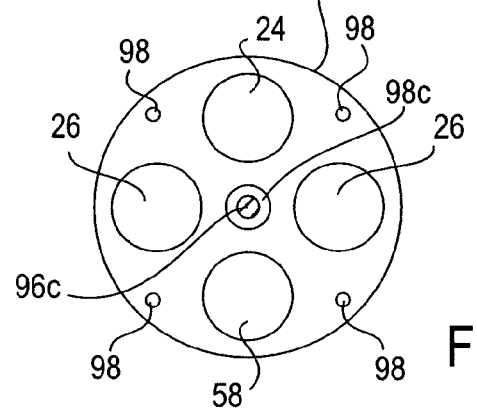
FIG. 10C illustrates the nestable elements of FIG. 10A with the inclusion of liners and FIG. 10D provides a cross-sectional view of one of the nestable elements.

In the embodiment illustrated in FIG. 9B, the nestable elements 260 have a central lumen 23 which passes through the length of the main body 10. Instruments or tools may be passed through this lumen 23, as indicated in FIGS. 9C-9D, or tubes may be present within the lumen 23 through which instruments or tools may be passed. In preferred embodiments, the nestable elements 260 have holes formed therein so that lumens are formed by alignment of the holes when the elements 260 are stacked. For example, FIG. 9E provides a cross-sectional view of a nestable element 260 illustrating the holes formed therein which serve as lumens. As shown, a scope lumen 24, arm guide lumens 26, and auxiliary lumens 58 extend through the center of the element 260 while pullwire lumens 98 are located around the periphery. It may be appreciated that pullwire lumens 98 may also extend through the center of the element 260. For example, FIG. 10A illustrates an embodiment having a pullwire 96 which extends through the center of the stacked nestable elements 260. FIG. 10A provides an exploded view of the nestable elements 260 wherein the elements 260 are disposed so that a distal surface 262 of one element 260 coacts with a proximal surface 264 of an adjacent element. As shown, each of the nestable elements 260 includes a pullwire lumen 98 through its center. FIG. 10B provides a cross-sectional view of a nestable element 260 of FIG. 10A. As shown, the nestable element 260 includes a locking pullwire lumen 98c having a pullwire 96c therethrough in the center of the element 260 surrounded by various other lumens, such as a scope lumen 24, arm guide lumens 26, auxiliary lumen 58 and various pullwire lumens 98 used for steering. Once the elements 260 are positioned in a desired arrangement, the shaft 20 may be locked in place by the central pullwire 96c. Applying tension to the pullwire 96c compresses the elements 260 to a state in which they are locked by friction wherein the tension is held.

Figure 10C:
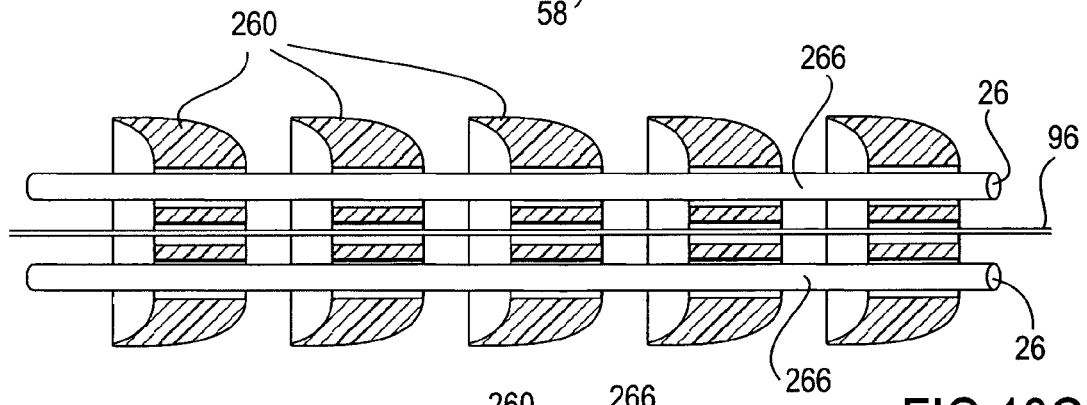
Figure 10D:
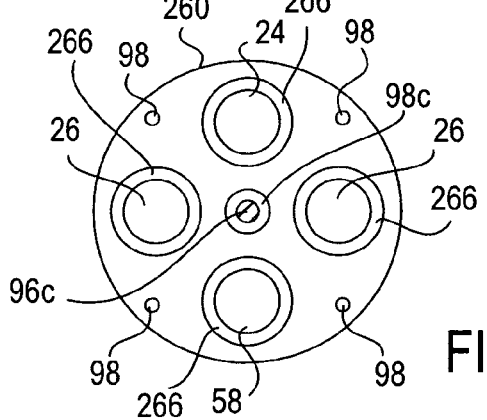

In addition, liners 266 may be passed through any of the lumens of the stacked nestable elements 260. Such liners 266 form create a continuous lumen connecting the lumen holes of the nestable elements 260. FIG. 10C illustrates the nestable elements 260 of FIG. 10A with the inclusion of liners 266 passing through, for example, the arm guide lumens 26. Likewise, FIG. 10D provides a cross-sectional view of a nestable element 260 of FIG. 10C. Here, liners 266 are shown positioned through the nestable element 260 forming lumens 24, 26, 58 therethrough. It may also be appreciated that liners 266 may extend through pullwire lumens 98 as well. The liners 266 may be coated on their luminal surface with a hydrophilic coating for reducing friction or the liners 266 may be comprised of a lubricious polymer such as Teflon®, fluoroethylene polymer (FEP) or the like.

It may be appreciated that the shaft 20 of the main body 10 may have any structure suitable for delivering the tool arms 30 to the desired location within the body. Exemplary embodiments of such structures are described above and provided in co-pending U.S. patent application Ser. No. 10/281, 462 filed Oct. 25, 2002, which is a continuation in part of U.S. patent application Ser. Nos. 10/173,203, 10/173,227, 10/173, 238 and 10/173,220, all of which were filed on Jun. 13, 2002 and herein incorporated by reference for all purposes. Also of interest and incorporated by reference for all purposes are co-pending U.S. patent application Ser. Nos. 10/281,461 and 10/281,426 each filed on Oct. 25, 2002. In addition, it may be appreciated that the main body 10 may be comprised of a traditional endoscope or laparoscope through which one or more tool arms 30 may be passed. Exemplary embodiments of traditional endoscopes are provided in U.S. Pat. Nos. 3,948,251; 4,036,218; 4,201,198; 4,224,929; 4,988,171; 5,020,539; 5,035,231; 5,068,719; 5,170,775; 5,172,225; 5,187,572; and 5,196,928, all of which are herein incorporated by reference for all purposes.

III. Tool Arms

Figure 11:
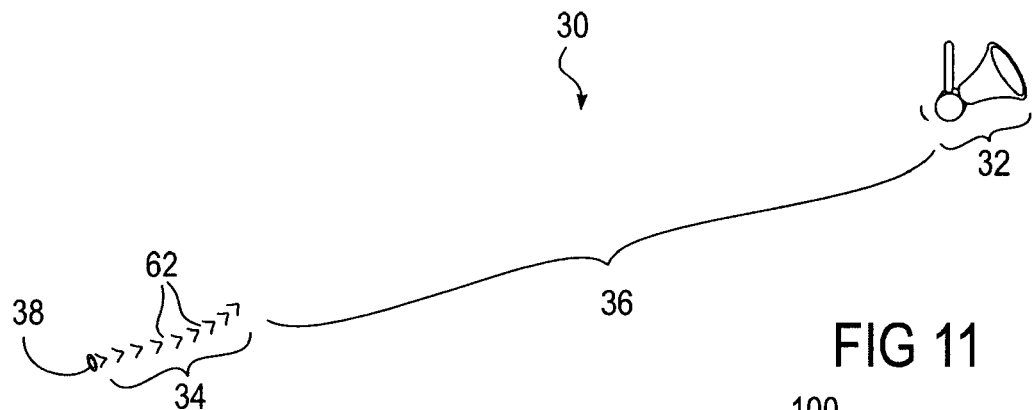
FIG. 11 illustrates an embodiment of a tool arm.

As mentioned previously, system 2 also includes at least one tool arm 30, each arm 30 of which is insertable through a separate arm guide lumen 26 in the main body 10. As shown in FIG. 11, each tool arm 30 has a proximal end 32, a distal end 34 and a shaft 36 therebetween. The distal end 34 is steerable, such as by manipulation of adjacent links 62 as schematically indicated. Such steerability may optionally be controlled by a steering cuff 35, disposed within the proximal end 32. Each tool arm 30 additionally includes a tool deployment lumen 38 therethrough.

A. Distal End

Figure 12A:
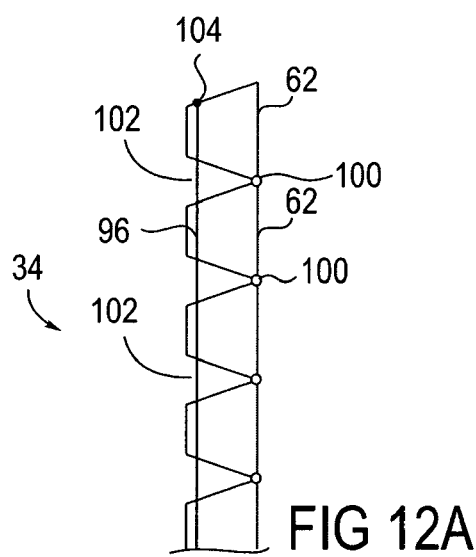
FIGS. 12A-12B, 13A-13B, 14 illustrate embodiments of adjacent links disposed at the distal end of a tool arm.
Figure 12B:
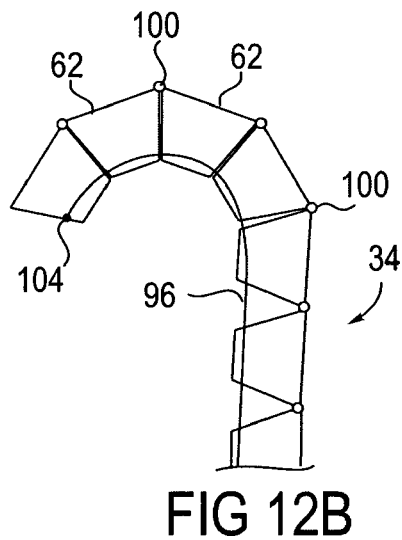

FIGS. 12A-12B illustrate an embodiment of adjacent links 62 disposed at the distal end 34 to allow steerability of the arm 30. Here, links 62 are pivotally connected by hinge structures 100. As shown in FIG. 12A, the links 62 are shaped so that connection by the hinge structures 100 creates gaps 102 between the links 62 directly opposite to the hinge structures 100. A pullwire 96 is shown extending through the links 62 and terminating at a fixation point 104. Referring now to FIG. 12B, retraction of the pullwire 96 draws the links 62 together, minimizing the gaps 102 between the links 62. Due to the shape and arrangement of the links 62, this movement creates a curve in the arm 30 as shown. The distal end 34 may be steered to have any curvature between substantially straight and a maximum curvature wherein the gaps 102 are completely closed or another limiting feature is established. In some embodiments, up to 360 degree curvature of the distal end 34 is possible. The distal end 34 may be returned to a straightened position by advancement of the pullwire 96 or by the presence of a spring which will straighten the distal end 34 by recoil force.

Figure 13A:
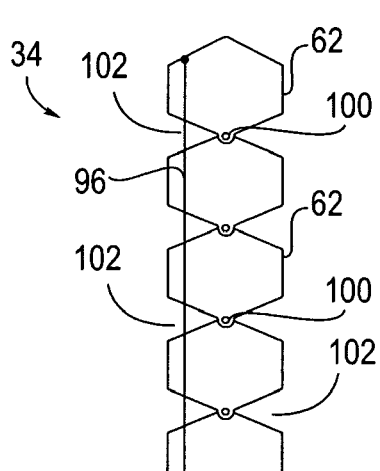
Figure 13B:
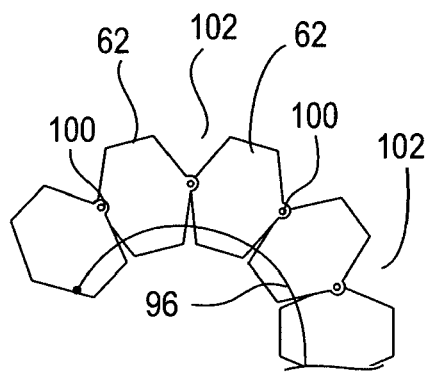

FIGS. 13A-13B illustrate a similar embodiment of adjacent links 62 disposed at the distal end 34 to allow steerability of the arm 30. Again, links 62 are pivotally connected by hinge structures 100. However, as shown in FIG. 13A, the links 62 are shaped so that connection by the hinge structures 100 creates gaps 102 between the links 62 on both sides of the hinge structures 100. A pullwire 96 is shown extending through the links 62 and terminating at a fixation point 104. Referring now to FIG. 13B, retraction of the pullwire 96 draws the links 62 together, minimizing the gaps 102 between the links 62 along the pullwire 96 and maximizing the gaps 102 on the opposite side of the hinge structures 100. Due to this shape and arrangement of the links 62, this movement creates a curve in the arm 30 as shown. The distal end 34 may also be returned to a straightened position by advancement of the pullwire 96 or by the presence of a spring which will straighten the distal end 34 by recoil force. However, in this embodiment, the distal end 34 may be deflected or curved in the opposite direction by continued advancement of the pullwire 96. Advancement of the pullwire 96 minimizes the gaps 102 on the opposite side of the hinge structures 100 causing a curvature in the opposite direction. Likewise, a spring may be present to straighten the distal end 34 from a curvature in this opposite direction.

Figure 14:
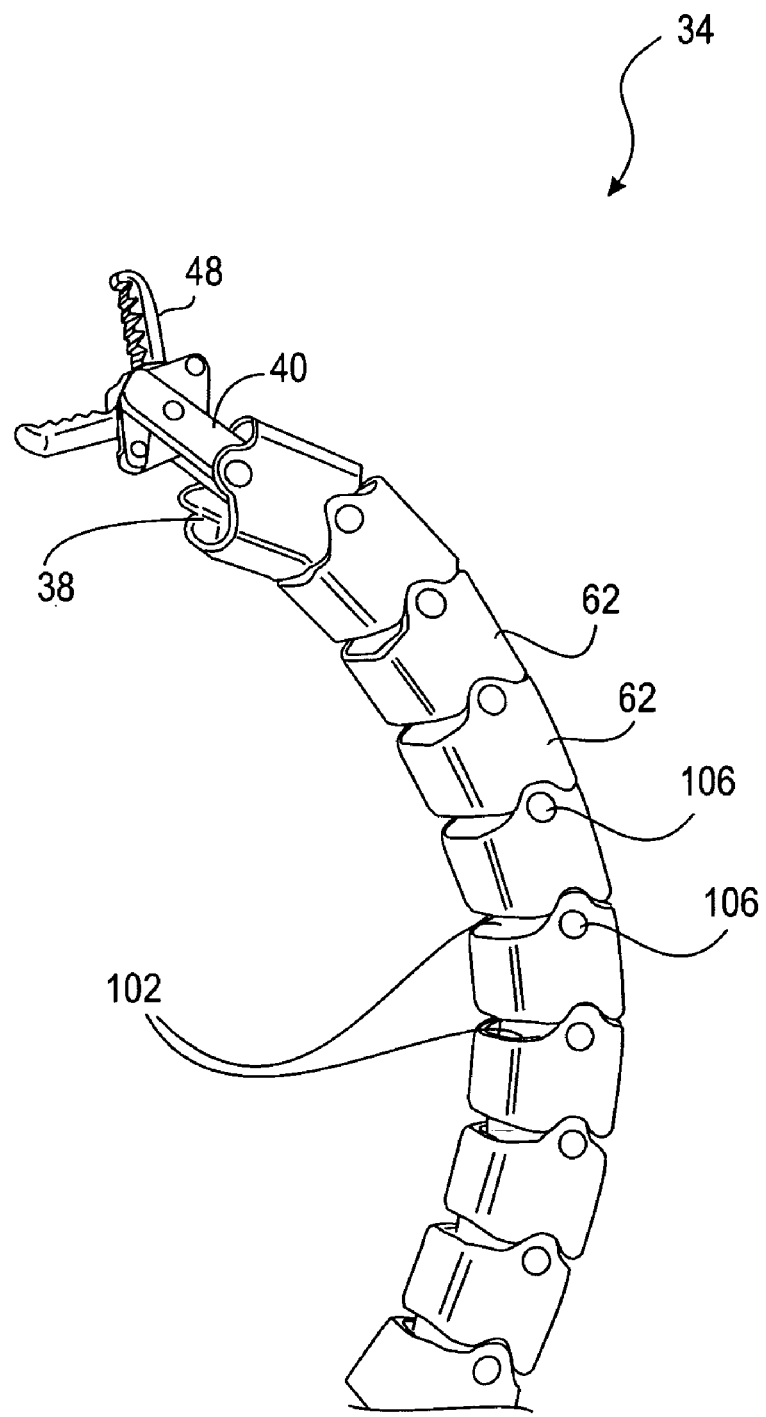

FIG. 14 illustrates an embodiment similar to the embodiment illustrated in FIGS. 13A-13B. The links 62 are shown pivotally connected by hinge structures 100. Here the hinge structures 100 comprise pivot pins 106 which are arranged in parallel to limit deflection to a single plane. In some embodiments, the hinge structures comprise male and female bearing surfaces which define axes, wherein the axes are disposed in parallel to limit deflection of the distal section to within the single plane. The links 62 are shaped so that connection by the pivot pins 106 creates gaps 102 between the links 62. Closure of the gaps 102 on one side of the pivot pins 106 simultaneously opens gaps on the other side of the pins 106. FIG. 14 also illustrates an end effector 48 of a tool 40 which has been advanced through the tool deployment lumen 38 of the arm 30.

Figure 15:
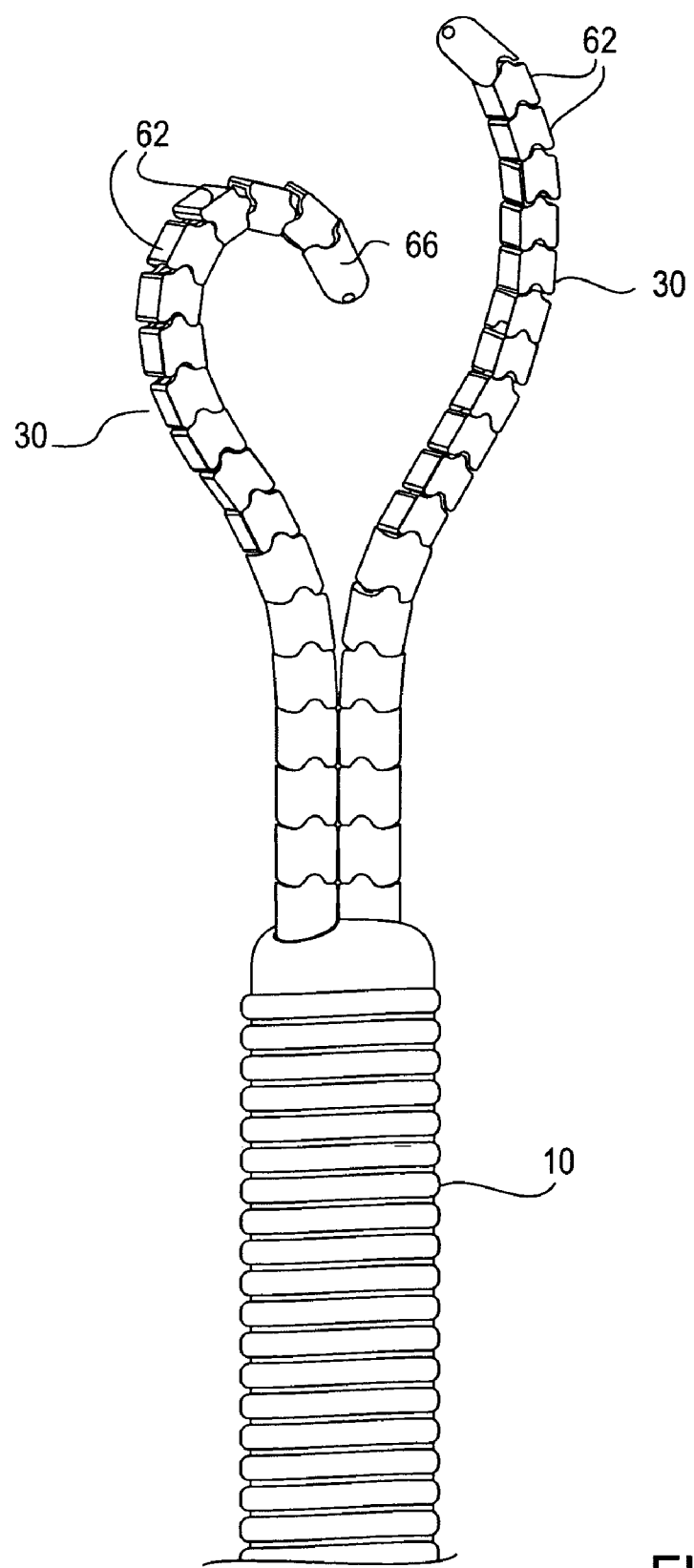
FIG. 15 illustrates examples of possible deflections or movements of an embodiment of the tool arm.

FIG. 15 illustrates examples of possible deflections or movements of the tool arms 30. Here, two arms 30 are shown emerging from the distal tip 16 of the elongated main body 10. The distal end 34 of each arm 30 is steerable and comprised of a plurality of adjacent links 62. The arm 30 on the left is shown steered to a position wherein the tip section 66 is curled inwardly forming an almost complete circular shape. In contrast, the arm 30 on the right is shown steered to a position wherein the tip section 66 is deflected slightly inwardly forming an arc shape. Thus, the arms 30 may be independently steerable to varying degrees of curvature. Preferably, the arms 30 are steerable inwardly to perform surgical procedures in cooperation and to maintain visibility through the centrally located scope.

Figure 16A:
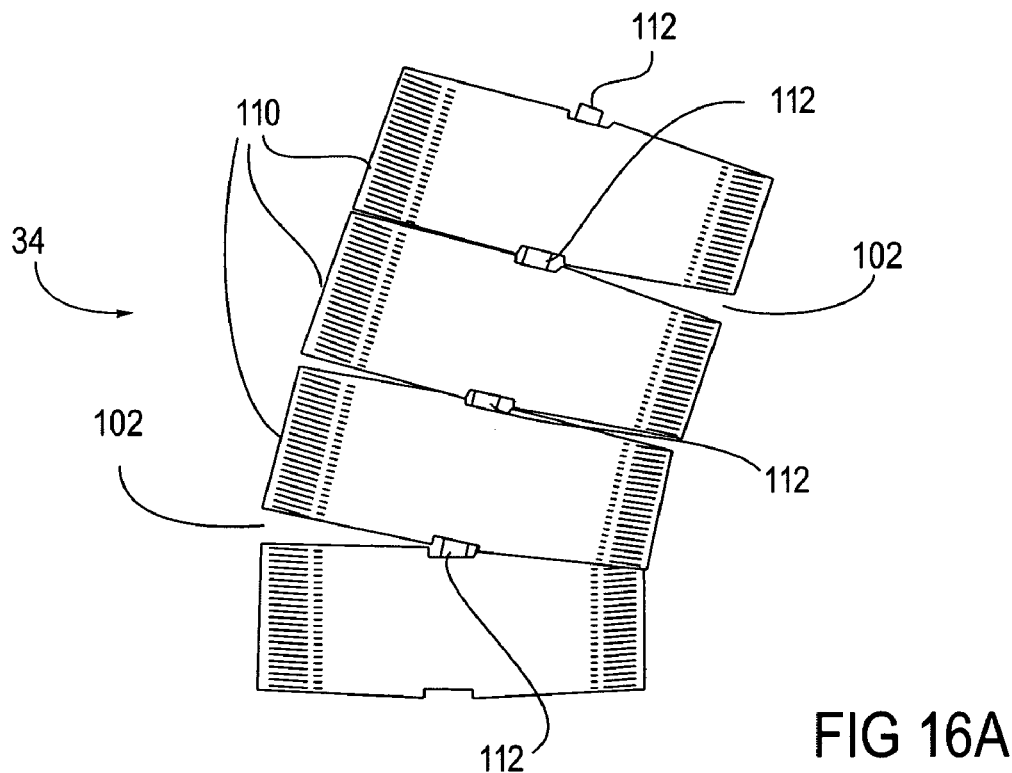
FIGS. 16A-16B illustrate another embodiment of a tool arm comprising a plurality of adjacent links.
Figure 16B:
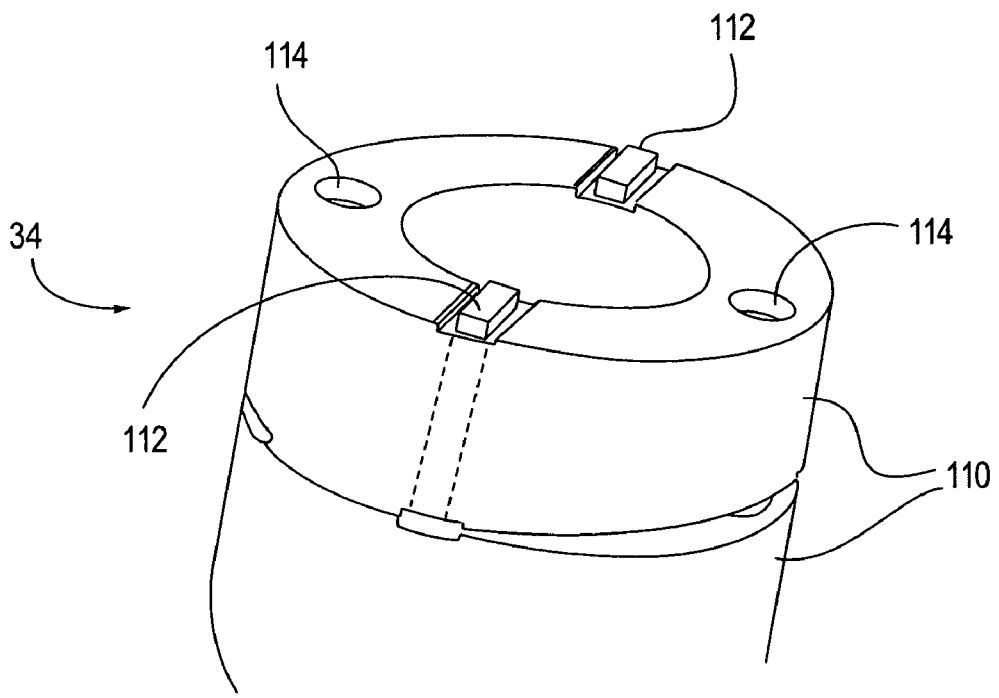

FIGS. 16A-16B illustrate another embodiment of a tool arm 30 comprising a plurality of adjacent links 62. Here, the links 62 are comprised of disks 110 having faces which are angled to form gaps 102 between the disks 110 when the disks 110 are stacked. The disks 110 are connected by one or more wires or ribbons 112. In this embodiment, illustrated in FIG. 16B, two ribbons 112 are present, each at diametrically opposite positions within the wall of each of the stacked disks 110 so that the angled faces are aligned between the ribbons 112. The ribbons 112 may be embedded in the wall, co-molded with the stacked disks or simply advanced through a lumen in the wall. The ribbons 112 maintain relative position of the disks 110 and stabilize the steerable distal end 34 to be deflectable in only a single plane. Also shown in FIG. 16B, lumens 114 are present between the ribbons 112 for positioning pullwires 96 therethrough. The pullwires 96 pass through the angled portions of the disks 110 so that application of tension to a pullwire 96 draws the angled faces of the disks 110 together to close the gaps 102 therebetween. This in turn widens the diametrically opposite gaps 102 creating curvature in the stack.

As mentioned previously, in some embodiments, the arms 30 are deflectable to form a predetermined arrangement, such as previously illustrated in FIG. 3D. Typically, when forming the predetermined arrangement, the arms 30 are steerable up until the formation of the predetermined arrangement wherein the arms 30 are then restricted from further deflection. FIG. 17 illustrates an embodiment of such an arm 30 comprising a plurality of adjacent links 62 wherein the arm 30 is steerable to a predetermined arrangement. As shown, the distal end 34 comprises a base 64 which deflects the distal end 34 outwardly and a tip section 66 which deflects inwardly. Between the base 64 and tip section 66 lies a spacer 68 which is rigid. The spacer 68 may be considered a larger elongate link or simply a straight section. Usage of such spacers 68 is optional and may be used to create specific predetermined arrangements. FIG. 17A is an enlarged view of the tip section 66 which illustrates the shapes of the links 62 which are pivotally connected by hinge structures 100 formed into the links 62. Gaps 102 are present on opposite sides of the structures 100 to allow curvature of the distal end 34. The size of the gaps 102 will vary due to varying sizes and shapes of the links 64 so that closure of the gaps 102 forms a specific curvature. This is most easily seen in FIGS. 17B-17C. FIG. 17B illustrates links 62 of the base 64 having varying shapes to create gaps 102 of varying size. As shown, a pullwire 96 extends through the links 62 along the gaps 102. Applying tension to the pullwire 96 draws the links 62 together to close the gaps 102 and to form a predetermined curve as in FIG. 17C.

The predetermined arrangement of FIG. 17 includes curvatures in opposite directions, the base 64 curving laterally outwardly and the tip section 66 curving laterally inwardly. These distinct curvatures may be achieved by separate pullwires 96. For example, as shown in FIG. 18A, a first pullwire 97a may be positioned along one side of the tool arm 30 terminating at a fixation point 104a located midway along the distal end 34. The links 62 which lie proximally of this fixation point 104a form the base 64. A second pullwire 97b may be positioned along the opposite side of the arm 30 terminating at a fixation point 104b located at the tip of the distal end 34. Generally, the links 62 which lie between the fixation point 104a and the fixation point 104b form the tip section 66. Referring now to FIG. 18B, by applying tension to the first pullwire 97a, the base curves laterally outwardly, and by applying tension to the second pullwire 97b, the tip section curves laterally inwardly.

FIG. 19 illustrates two tool arms 30 which are steered to a predetermined arrangement. Such steering is achieved with the use of pullwires 96 as illustrated in FIGS. 18A-18B. Fixation points 104b are visible while fixation points 104a are hidden within the arms 30. As shown, the links 62 are varied in size and shape to form this arrangement when tension is applied to the pullwires 96. For example, the links 62 are generally larger thought the bases 64 and smaller through the tip sections 66. Further, this embodiment includes stabilizers 120 which pass through the arms 30 for stability.

In some embodiments, the steerable distal end 34 includes both types of links, links which are steerable to a predetermined arrangement and links which are unrestrictedly steerable. For example, FIG. 20 illustrates an embodiment wherein the base 64 is comprised of links 62 which are appropriately shaped and sized to deflect laterally outwardly to form a predetermined arrangement. Such deflection is achieved with a pullwire which is hidden from view and terminates midway along the distal end 34. In this embodiment, the tip section 66 is comprised of links 62 which are appropriately sized and shape to deflect laterally inwardly in an unrestricted fashion. The links 62 of the tip section 66 are hinged together by pivot pins 106 to provide support throughout the unrestricted movement. In addition, a tool 40 having an end effector 48 is shown passed through the tool deployment lumen 38 in the arm 30. Also shown in FIG. 20, the arms 30 are rotated to lie in different planes, a feature which has been described in previous sections.

It may be appreciated that the embodiments which include links may have any number of links. For example, the steerable distal end 34 may have two links 62 which are hinged together by a hinge structure 100. In this example, the shaft 36 would direct the first link 62 in a first direction and the hinge structure 100 would turn the distal tip 16 towards a second direction. The addition of more linkages 62 would create a smoother curve and/or allow multiple curves throughout the steerable distal end 34.

Although the previous embodiments of the tool arms 30 have been comprised of a plurality of adjacent links, it may be appreciated that the arms 30 may be comprised of material in any suitable form. For example, each arm 30 may be comprised of a polymeric tube which has been pre-shaped, such as by heat setting, to form a desired curvature. The polymeric tube is comprised of a material which is sufficiently flexible to allow straightening of the curve for delivery through the arm guide lumen 26 and adequately flexible to allow recoiling of the arm 30 to form the desired curvature upon emergence from the lumen 30.

In another embodiment, each arm 30 is comprised of a slotted tube, as illustrated in FIGS. 21A-21B. Referring to FIG. 21A, a tube 130 has a series of slots 132 along its length. In this embodiment, the slots 132 are present along one side of the tube 130 however, it may be appreciated that the slots 132 may be present on both sides of the tube or along any portion of the tube which is desired to deflect. Referring back to FIG. 21A, the pullwire 96 is positioned within the tube along the slots 132 and fixed to the tube 130 at a fixation point 104. By applying tension to the pullwire 96, the tube 130 is deflected toward the pullwire 96 as shown in FIG. 21B. The presence of the slots 132 allows the tube 130 to be comprised of a relatively rigid or thick material while deflecting and curving with minimal buckling or impedance by the tube 130. It may be appreciated that the tube 130 of FIGS. 21A-21B may alternatively be a solid-walled tube without slots comprised of a thinner or more flexible material which itself allows deflection and curvature with minimal buckling or impedance. Further, each of the following embodiments illustrating various tool arms 30 may be comprised of solid-walled or slotted tubes, or any other suitable tube construction.

Figure 21C:
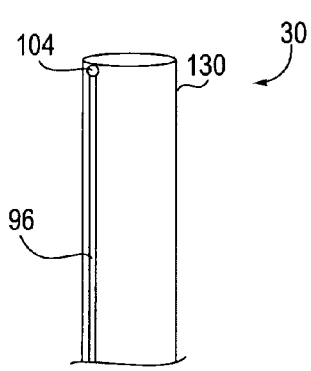
FIGS. 21C-21D illustrate an embodiment of a tool arm comprised of a tube wherein a pullwire is positioned on the outside of the tube.
Figure 21D:
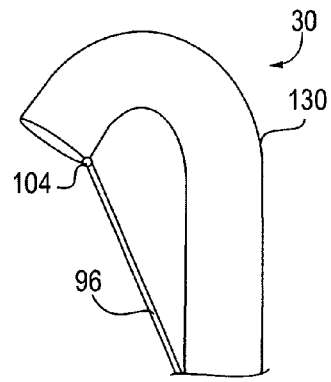

FIGS. 21C-21D illustrate an embodiment of the arm 30 comprised of a tube 130 wherein a pullwire 96 is positioned on the outside of the tube 130 and fixed to the tube 130 at a fixation point 104. By applying tension to the pullwire 96, the tube 130 is deflected toward the pullwire 96 as shown in FIG. 21D. Since the pullwire 96 is disposed outside of the tube 130, the pullwire 96 forms a tether to the fixation point 104 and does not follow along the surface of the tube 130.

Figure 21E:
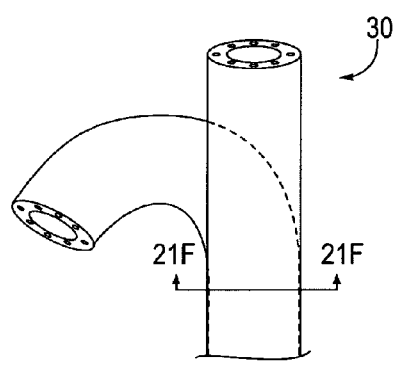
FIGS. 21E-21F illustrate an embodiment of a tool arm comprised of a polymer wall co-extruded with shape memory material.
Figure 21F:
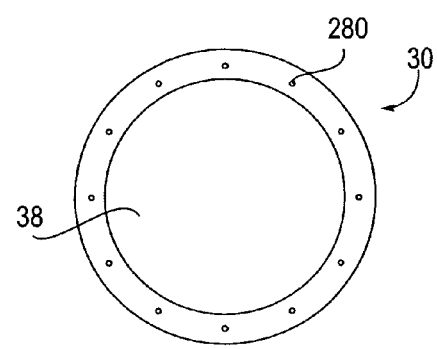

FIGS. 21E-21F illustrate an embodiment of the arm 30 comprised of a polymer wall co-extruded with shape memory material, such as nitinol wire. FIG. 21E illustrates the arm 30 in a straightened position, wherein the arm 30 is passed through the arm guide lumen 26, and a curved position, wherein the arm 30 recoils to a shape-memory curve. FIG. 21F provides a cross-sectional view of the arm 30 of FIG. 21E illustrating shape-memory material 280 distributed within the wall of the arm 30.

Figure 21G:
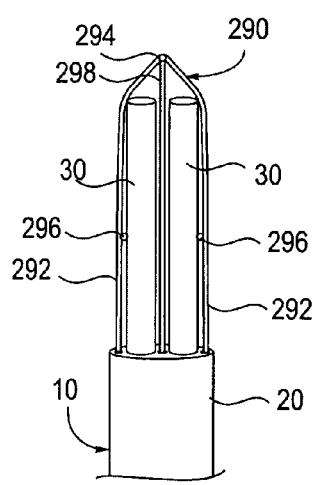
FIGS. 21G-21H illustrate a mechanism for steering the tool arms including a deployment frame.
Figure 21H:
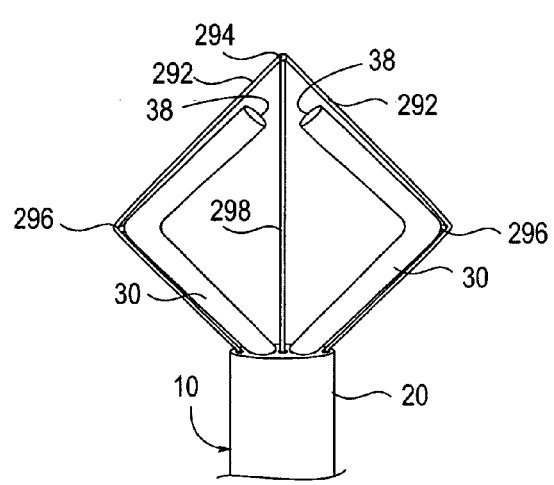

FIGS. 21G-21H illustrate an alternative mechanism for steering the tool arms 30. Referring to FIG. 21G, the shaft 20 of the main body 10 is illustrated having a pair of tool arms 30 extending therefrom. Surrounding the arms 30 lies a deployment frame 290. The frame 290 is comprised of a semi-rigid or rigid material, such as stainless steel wire, which provides sufficient strength to apply force to the arms 30. The frame 290 comprises at least two supports 292, each extending from the distal tip 16 of the shaft 20 and connecting at a peak 294. Each support 292 attaches to a tool arm 30 at an attachment point 296. The frame 290 also includes an actuation support 298 extending from the distal tip 16 to the peak 294. The arms 30 and supports 292, 298 advance from the distal tip 16 of the main body 10 to a desired location in the body in a straight configuration as illustrated in FIG. 21G. Referring to FIG. 21H, application of tension to the actuation support 298 draws the peak 294 toward the distal tip 16 causing the supports 292 to bow or bend outward drawing the attached arms 30 outward. Likewise, the supports 292 may include hinges wherein the supports 292 would bend at the hinge. Although FIG. 21H illustrates the arms 30 bending at the attachment points 296, it may be appreciated that the arms 30 may bend at any location. Such bending directs the tool deployment lumens 38 toward each other to facilitate coordination of tools passed therethrough. Movement of the peak 294 proximally and distally varies the curvature of the arms 30 and provides steering. The frame 290 also serves to create a working space, restricting surrounding tissue from encroaching on the arms 30 and tools 40.

In most embodiments, the distal ends of the tool arms are lockable to maintain a deflected position. Such locking may be achieved by any suitable mechanisms. When the tool arm is steerable by manipulation of pullwires or pushwires, the wires may be held in place to lock the distal end in a desired position. In embodiments comprising a multiplicity of nestable elements through which pullwires pass, the pullwires are typically used to hold the elements in nesting alignment and to provide steering and locking. By applying tension to the pullwires simultaneously, the elements may be compressed to a state in which they are locked by friction wherein the tension is held. Other locking mechanism may also be used. Further, the tool arms may be locked rotationally and axially within the main body to maintain positioning of the tool arm in relation to the main body.

B. Shaft

As described previously, the shaft 36 of the tool arm 30 passes though the main body 10. In embodiments wherein the main body 10 is deflectable, the shaft 36 is also deflectable. However, although it is desired that the shaft 36 be laterally deflectable, it is also desired that the shaft 36 maintain axial rigidity. Any suitable construction may be used, including a braid reinforced torqueable tube. Additional embodiments are described below.

Figure 22A:
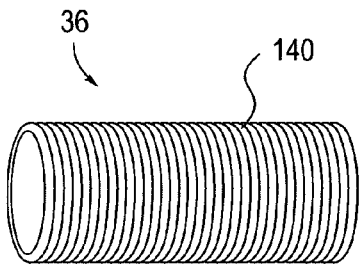
FIGS. 22A-22B, 23, 24 illustrate embodiments of the shaft of the main body.
Figure 22B:
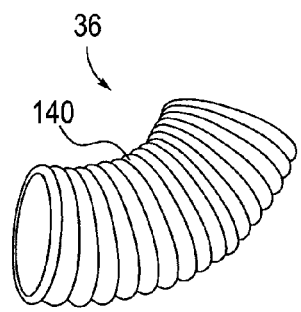

FIGS. 22A-22B illustrate embodiments of the shaft 36 comprising a coil 140. Here, illustrated in FIG. 22A, the turns of the coil 140 lie adjacent to each other to prevent axial movement and maintain axial rigidity. However, the coil configuration allows deflection of the shaft 36 as shown in FIG. 22B.

Figure 23:
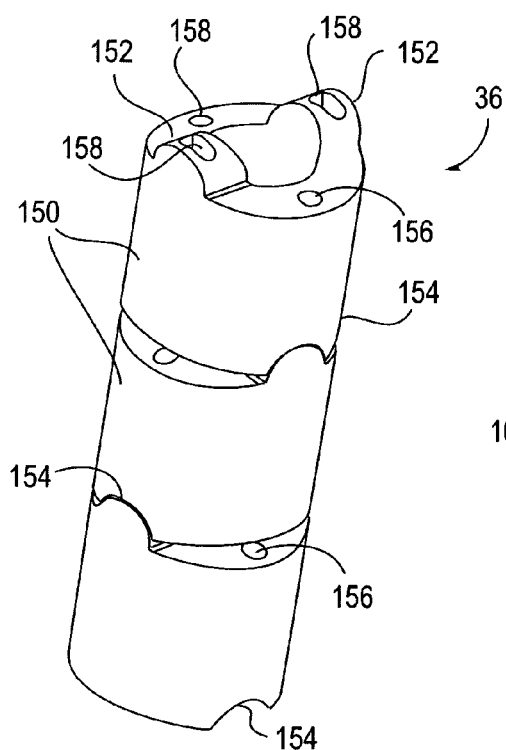

In another embodiment, illustrated in FIG. 23, the shaft 36 comprises a plurality of adjacent linkages 150. Here, each linkage 150 includes a pair of protruding structures 152 on its face and a pair of notches 154 on its base. The protruding structures 152 and notches 154 are both arc shaped so that the protruding structures 152 of one linkage 150 rotateably interfit with the notches 154 of an adjacently stacked linkage 150. By alternating the position of the pairs of protruding structures 152 and notches 154 as shown in FIG. 23, the shaft 36 is flexible in both lateral bending directions while maintaining stiffness axially and in torsion. Also shown are flared lumens 158 which pass through the protruding structures 152 and the wall of the shaft 36. Flaring allows for a rod or wire passed therethrough to move within the lumen 158 as a linkage 150 rotates over the protruding structure 152. Round pullwire lumens 156 pass through the notches 154 and the wall of the shaft 36 as shown. The rod or wire holds the linkages 150 in a stacked configuration and optionally may be used to steer the shaft 36.

Figure 24:
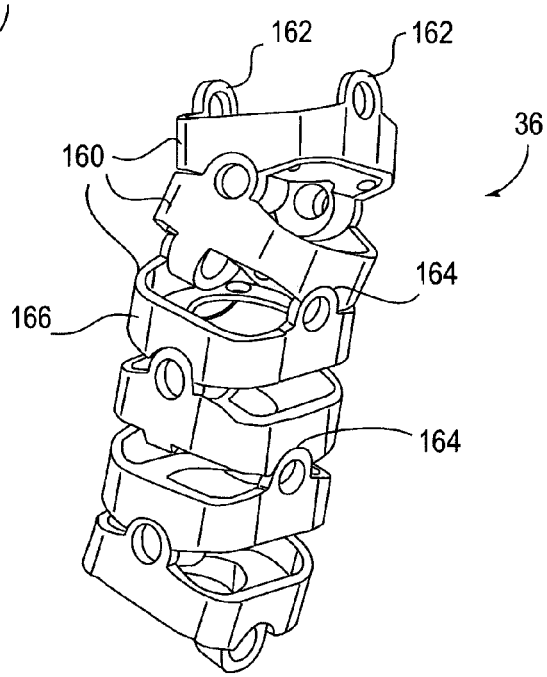

In another embodiment, illustrated in FIG. 24, the shaft 36 comprises a plurality of adjacent linkages 160 which are also stacked to provide lateral deflection while maintaining axial rigidity. Here, each linkage 160 includes a pair of protruding structures 162 on its face and a pair of notches 164 on its base. The protruding structures 162 and notches 164 are both arc shaped so that the protruding structures 162 of one linkage 160 rotateably interfit with the notches 164 of an adjacently stacked linkage 160. By alternating the position of the pairs of protruding structures 162 and notches 164 as shown in FIG. 24, the shaft 36 is flexible in both lateral bending directions while maintaining stiffness axially and in torsion. In this embodiment, the linkages 150 include a central lumen 166 through which a rod or wire is passed. The rod or wire is used to hold the linkages 60 in the stacked configuration.

C. Proximal End

The proximal end 32 of the tool arm 30 may simply terminate in an endpiece or connector for passage of a tool 40 through its tool deployment lumen 38. However, the proximal end 32 may optionally include a steering cuff 35 for steering the tool arm 30, particularly for steering its distal end 34.

Figure 25A:
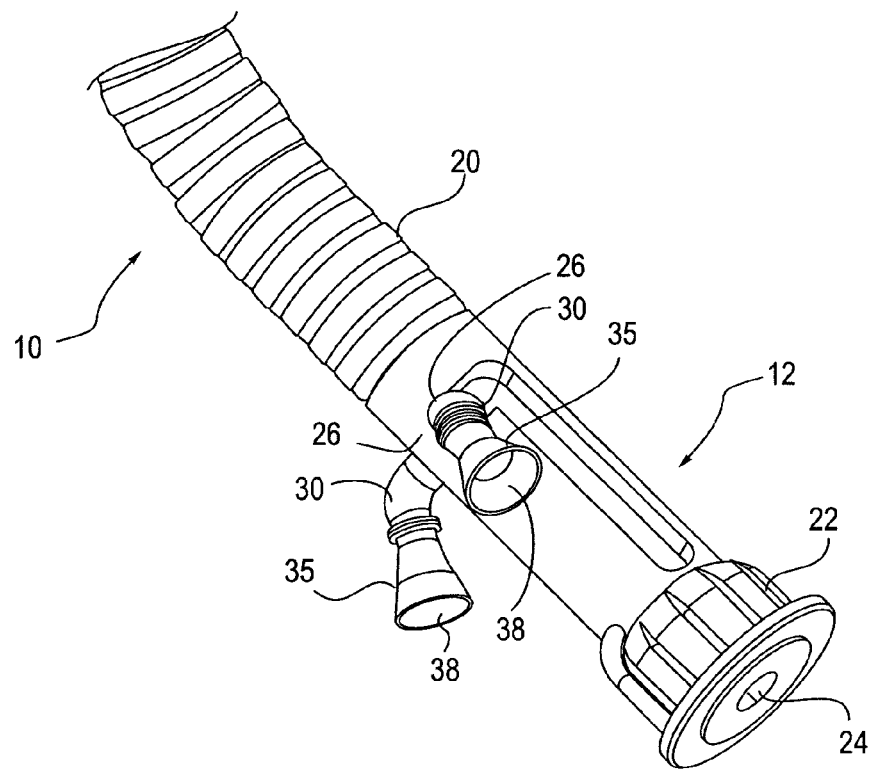
FIGS. 25A-25B provide a view of the proximal end of an embodiment of the main body wherein two tool arms are present, each including a steering cuff.
Figure 25B:
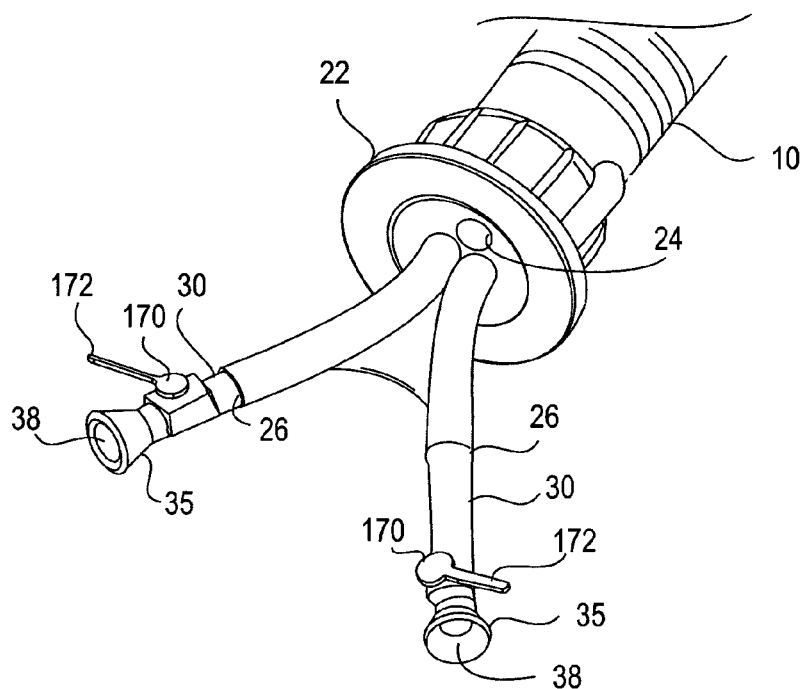

FIG. 25A illustrates an embodiment of the proximal end 12 of the main body 10 wherein two tool arms 30 are present, each inserted through an arm guide lumen 26 in the shaft 20 of the main body 10. As shown, each tool arm 30 includes a steering cuff 35 which remains outside of the main body 10 and the tool deployment lumen 38 is accessible through the steering cuff 35. FIG. 25B illustrates an alternative embodiment of the proximal end 12 wherein two tool arms 30 are present, each inserted through an arm guide lumen 26 through the handle 22 of the main body 10. Again, each tool arm 30 includes a steering cuff 35 which remains outside of the main body 10 and the tool deployment lumen 38 is accessible through the steering cuff 35. This embodiment also includes a locking mechanism 170 on each arm 30. The locking mechanism 170 can be manipulated, such as by turning a lever 172 shown in FIG. 25B, to lock the distal end 34 or the tool arm 30 in a steered or deflected position.

Figure 26:
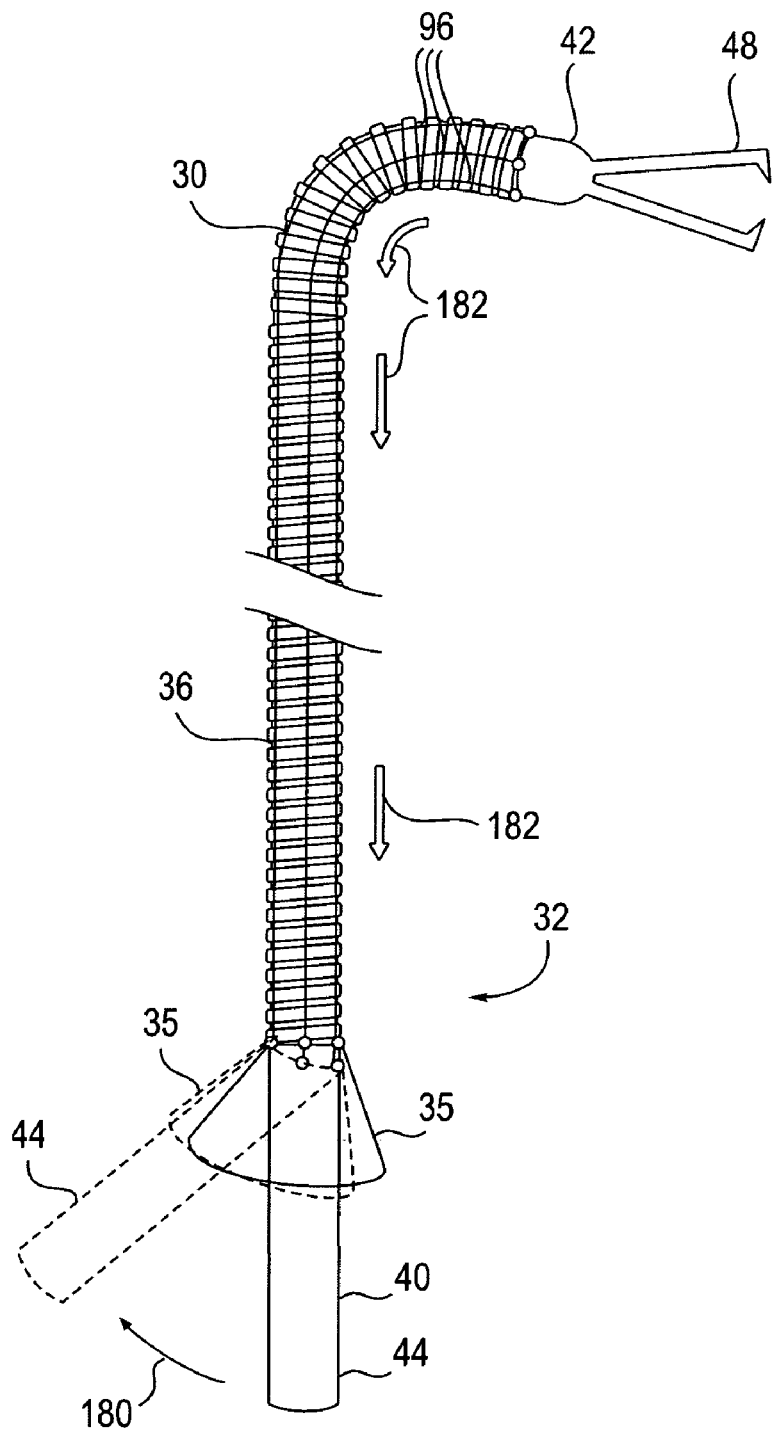

FIG. 26 illustrates an embodiment of a steering cuff 35 disposed at the proximal end 32 of a tool arm 30 wherein a tool 40 is passed therethrough. In this embodiment, the tool arm 30 includes four pullwires 96 (three are visible in FIG. 26) which are equidistantly positioned around the perimeter of the shaft 36. The pullwires 96 are used to steer the distal end 34 of the arm 30 as previously described. As shown, the tool 40 has a distal end 42 with an end effector 48 which emerges from the distal end 34 of the arm 30. Likewise, the tool 40 has a proximal end 44 which emerges from the steering cuff 35. In this embodiment, the steering cuff 35 has a funnel shape wherein one end is attached to at least the pullwires 96 and typically additionally to the arm 30 itself. Deflection of the proximal end 44 of the tool 40, indicated by angular arrow 180, presses the proximal end 44 against the steering cuff 35 which rotates the steering cuff 35 to a deflected position, indicated by dashed line. Such rotation applies tension to pullwires 96 diametrically opposite to the deflected position as indicated by arrows 182. Such tension steers the distal end 34 of the arm 30. Thus, manipulation of the tool 40 within the steering cuff 35 can be used to steer the distal end 34 of the arm 30.

Figure 28A:
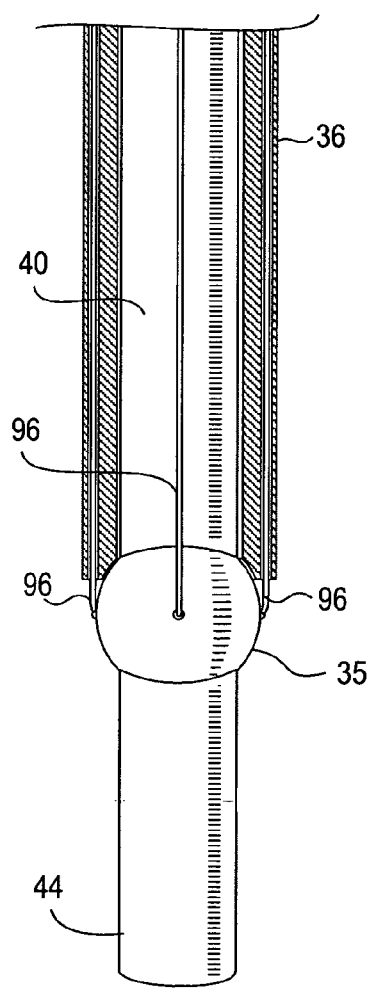
Figure 28B:
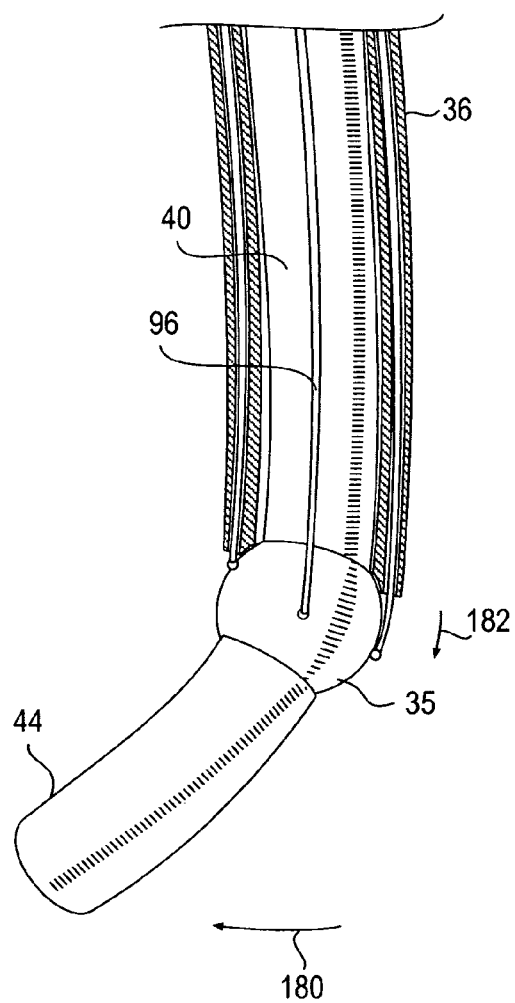

FIGS. 27A-27B and FIGS. 28A-28B illustrate another embodiment of a steering cuff 35. Here, the steering cuff 35 has a sphere shape and is disposed at the proximal end 32 of the tool arm 30. The tool 40 is passed through a lumen 184 in the sphere shaped cuff 35 so that the distal end 42 of the tool emerges from the distal end 34 of the arm 30 and the proximal end 44 remains outside of the cuff 35 as shown. In this embodiment, the tool arm 30 includes four pullwires 96 (three are visible) which are equidistantly positioned around the perimeter of the shaft 36. The pullwires 96 are used to steer the distal end 34 of the arm 30 as previously described. FIG. 27A illustrates the pullwires 96 emerging from the shaft 36 of the arm 30 and attached to the surface of the sphere shaped cuff 35. Likewise, FIG. 27B provides a similar view, however in this case the arm 30 is cutaway to reveal the pullwires 96 extending through lumens in the shaft 36 and the tool 40 extending through the tool deployment lumen 38. FIG. 28A illustrates the embodiment in the straight position. Deflection of the proximal end 44 of the tool 40, indicated by angular arrow 180, presses the proximal end 44 against the steering cuff 35 which rotates the steering cuff 35 to a deflected position, as shown in FIG. 28B. Such rotation applies tension to pullwires 96 diametrically opposite to the deflected position as indicated by arrow 182. Such tension steers the distal end 34 of the arm 30. Thus, manipulation of the tool 40 within the steering cuff 35 can be used to steer the distal end 34 of the arm 30.

It may be appreciated that the embodiments of the steering cuff 35 depicted in FIG. 26 and FIGS. 27A-27B, 28A-28B may include any number of pullwires 96 for any desired level of steerability. For example, in each embodiment, two pullwires 96 may be present disposed on opposite sides of the steering cuff 35 for movement of the steerable distal end 34 of an arm 30 in a single plane. This would be the case for laterally stabilized arms 30.

IV. Tool

As mentioned previously, the system 2 also includes at least one tool 40. In some embodiments, the tool 40 may simply comprises an end effector 48 positioned at the distal end of the tool arm 30 wherein the end effector 48 is operated by manipulation of mechanisms which extend through the arm 30. In other embodiments, each tool 40 includes a distal end 42, a proximal end 44 and an elongate shaft 46 therebetween to allow passage through the tool deployment lumen 38 of the arm 30. The shaft 46 is typically desired to be a torque-stable tube comprised of any suitable material, such as a braid or coil-reinforced extrusion. In these embodiments, each tool 40 has an end effector 48 disposed at the distal end 42 and optionally a handle 50 at the proximal end 44 for manipulation of the end effector 48 from outside the body. Thus, the tool 40 is advanced so that the end effector 48 emerges from the distal end 34 of the arm 30.

A wide variety of end effectors 48 may be used depending on the procedure or tissue manipulations which are desired. For example, end effectors 48 may include but are not limited to knives, needles, sutures, staplers, fasteners, clippers, electrosurgical or hemostatic cutters and coagulators, laser welders, cryosurgery instruments, secondary scopes, forceps, lasers hooks, tongs, graspers, retractors, probes, clamps, scissors, tissue approximation devices and suction applicators.

Figure 29:
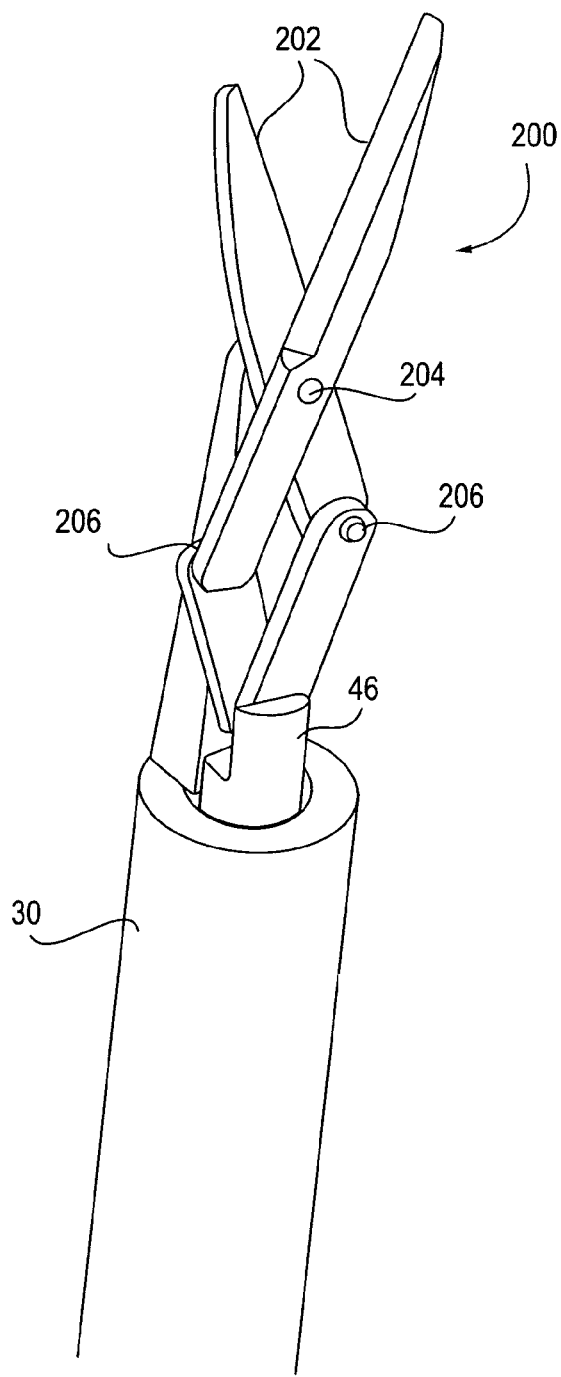
FIGS. 29, 29A-29D illustrate embodiments of a tool having an end effector in the form of various types of scissors.

FIG. 29 illustrates an embodiment of a tool 40 having an end effector 48 in the form of scissors 200. Scissors are one of the oldest surgical instruments used by surgeons. Scissors are used to perform many tasks in open surgical procedure but its use in minimal access surgery requires greater skill. As shown, the scissors 200 includes two blades 202, a fulcrum 204 and force applicators 206. The cutting force of the scissors 200 works on the law of lever. The force applied on the blade 202 can be calculated by length of the force applicators 206 and force applied on the applicators 206. The scissors 200 of the tool 40 do not apply the exact law of lever because of the cylinder action of the long shaft 46, but the design of applicators 206 helps in the amplification of force by lever action. When the blades 202 of the scissors 200 close, its sharp edges grind against each other and any tissue which comes between the blades of scissors will be cut.

Figure 29A:
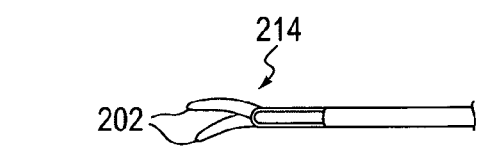
Figure 29B:
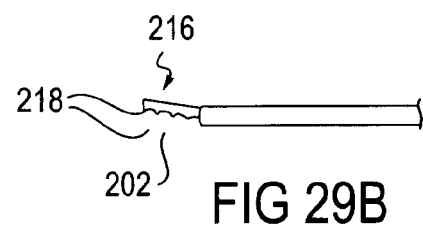
Figure 29C:
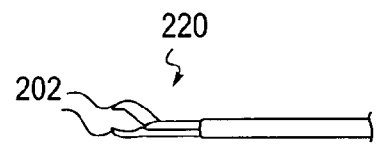
Figure 29D:
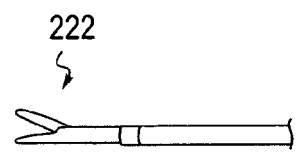

The scissors 200 of FIG. 29 provide an example of straight scissors wherein the blades are straight. This is a widely used instrument for mechanical dissection in laparoscopic surgery. Other types of scissors include curved scissors 214, illustrated in FIG. 29A, wherein the blade 202 of the scissors 214 is slightly curved. In some cases curved scissors 214 are preferred because the curvature of the blade 202 of this scissors creates additional angles of manipulation and may provide a better view through the scope. Other types of scissors include serrated scissors 216 wherein serrated edges 218 prevent the tissue from slipping out of the blades 202. This may be useful in cutting a slippery tissue or ligature. Still other types of scissors include hook scissors 220 which encircle a tissue structure before cutting. Since the tissue is held between its hooked blades, there is minimal chance of slipping. The hook scissor 220 is especially useful for cutting secured ducts or arteries. Likewise, the cutting of nerve bundles in neurectomy becomes may benefit from the use of hook scissors 220. Hook scissors 220 are also helpful in partial cutting of cystic ducts for intra-operative cholangiography. Further, additional types of scissors include microtip scissors 222. One of the main advantages of microtip scissors 222 is to cut ducts partially for facilitating cannulation. Likewise, this scissor 222 may be used for cutting the cystic duct for performing intra-operative cholangiogram. Exploration of small ducts like common bile duct is very helpful with microtip scissors 222 due to its fine small blades. Fine microtip scissors 222 are also available in curved form.

FIG. 30 illustrates an embodiment of a tool 40 having an end effector 48 in the form of gator toothed graspers 230. These graspers 230 have reverse angled teeth 232 which are capable of providing an aggressive grip on tissue. In addition, the graspers 230 are cupped to allow tissue to herniated when the tissue is compressed. Thus, the graspers 230 may be useful for pelviscopy and handling fibrous ovaries and uterine tissue.

FIG. 31 illustrates an embodiment of a tool 40 having an end effector 48 in the form of an articulatable grasper 236. The grasper 236 includes an articulation section 238 between grasper jaws 240 and the shaft 46. This allows the grasper 236 to articulate in an additional degree of freedom relative to tool arm 30.

Figure 35:
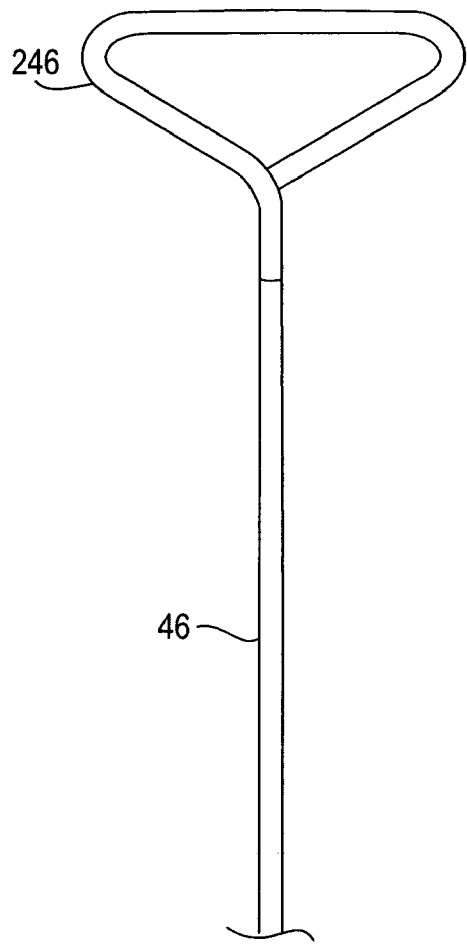
Figure 36:
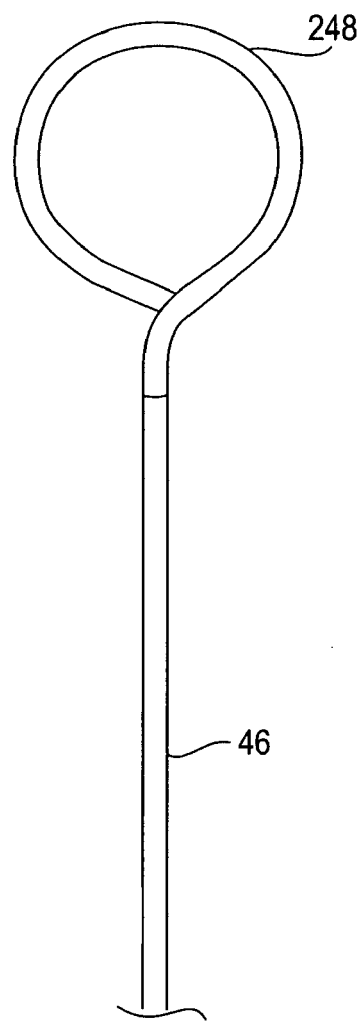

Embodiments of the tool 40 having an end effector 48 may be in the form of various shaped retractors. Examples of such retractors include an angled retractor 242, (FIG. 32), hooked retractors 244 (FIGS. 33-34), a triangular retractor 246 (FIG. 35), and a circular retractor (FIG. 36), to name a few. Each retractor is flexible and allows for manipulation of organs and tissue structures.

V. Auxiliary Lumens

As mentioned previously, lumens in addition to the scope lumen 24 and arm guide lumens 26 may be present within the main body 10 and may be considered auxiliary lumens 58. Such lumens 58 may be used for any purpose, such as irrigation, suction, insufflation, macerating, illuminating, grasping, or cutting to name a few, and are typically used in conjunction with the arms 30 and/or tools 40 inserted through the arms 30 or positioned at the ends of the arms 30.

In one embodiment, illustrated in FIG. 37A, grasping hooks 310 are inserted through a single auxiliary lumen or through separate auxiliary lumens 58 (shown) in the shaft 20. The grasping hooks 310 may be comprised of any suitable material, such as shape-memory wire or shapeable polymer, that allows a hook shape to be formed once the hooks 310 have emerged from the distal tip 16. In addition, the hooks 310 may have a pointed or sharp tip to assist in grasping or piercing tissue. Referring to FIG. 37B, the grasping hooks 310 may be used to grasp a portion of tissue T to create a plication or fold. The tool arms 30 may then be extended on opposite sides of the folded tissue T to deploy a fixation device 312 which will hold the plication in place. FIG. 37C illustrates such a fixation device 312 comprising a tie 314 passing through the tissue T with anchors 316 positioned on either side of the plication. The tie 314 may be comprised of a suture, wire or rod, for example, and the anchors 316 may be comprised of knots, disks or expandable umbrellas, to name a few. Such plication procedures may be used for treating gastroesophageal reflux disease (GERD).

Figure 38:
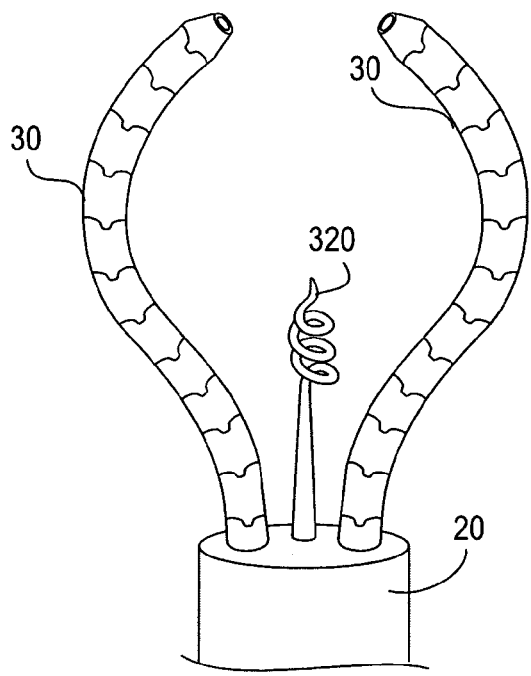
FIGS. 38, 39, 40A-40B illustrate alternative tools passed through auxiliary lumens in the main body.
Figure 39:
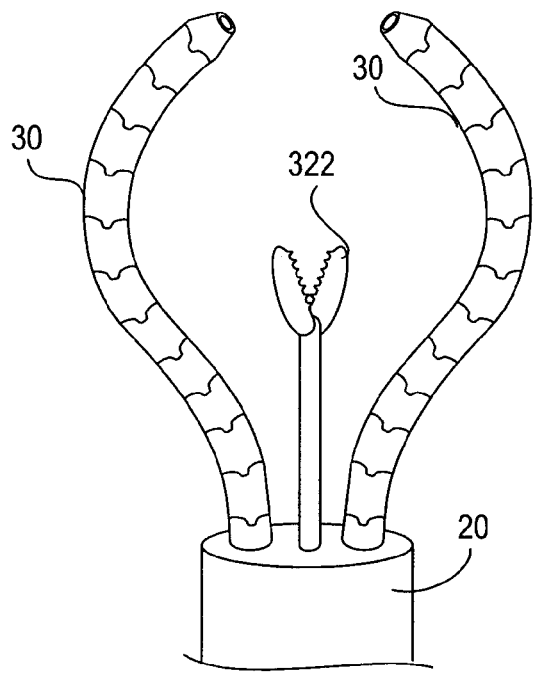
Figure 40A:
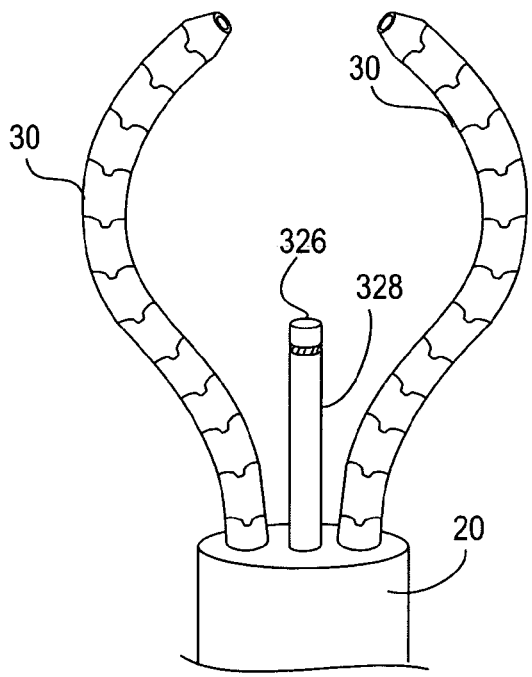
Figure 40B:
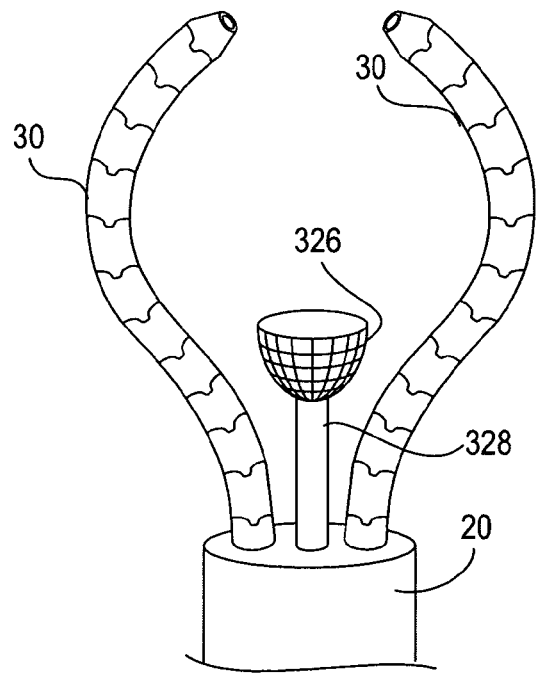

Alternatively, other tools may be passed through auxiliary lumens 58 for similar or other purposes. For example, a corkscrew device 320 (FIG. 38) or a grasper claw 322 (FIG. 39) may be passed through an auxiliary lumen 58 for grasping tissue T. Or, tissue T may be grasped with a suction device. FIG. 40A illustrates a suction device 324 in an undeployed configuration. The suction device 324 comprises a deployment sleeve 328 which houses an expandable funnel 326. Withdrawal of the deployment sleeve 328 releases the funnel 326 allowing the funnel 326 to self-expand, as shown in FIG. 40B. The increased surface area of the funnel 326 allows for adequate suction for grasping tissue T and holding the tissue T within the funnel 326.

Figure 41:
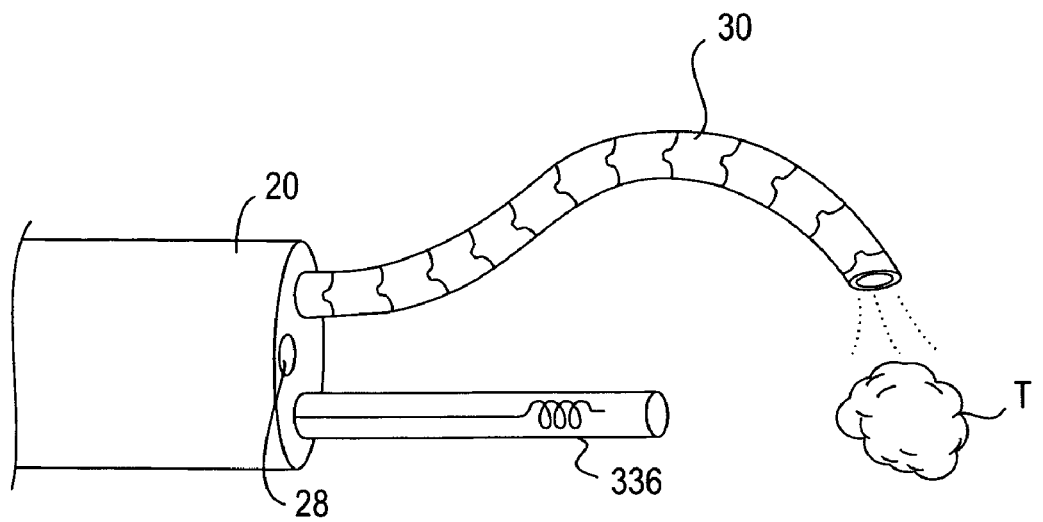
FIG. 41 illustrates a tool passed through an arm guide lumen for use in conjunction with a tool arm.
Figure 42:
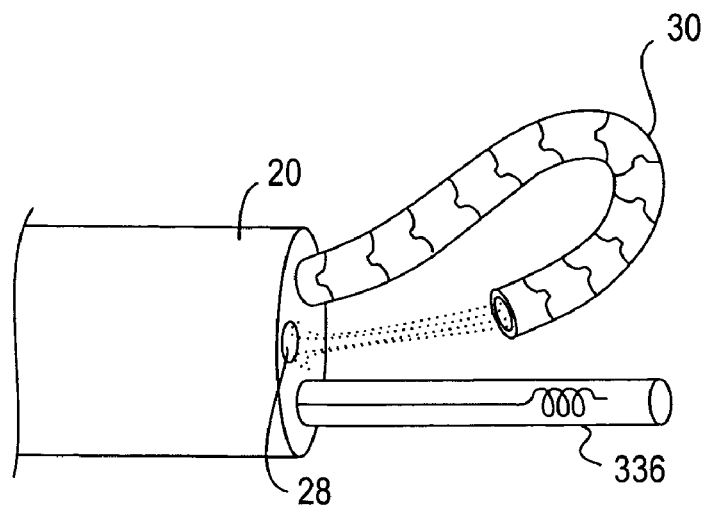
FIG. 42 illustrates an arm used to cleanse a portion of the main body, particularly the scope lens.

It may be appreciated that tools 40 may alternatively be passed through an arm guide lumen 26 for use in conjunction with a tool arm 30 passed through another arm guide lumen 26. For example, as illustrated in FIG. 41, a macerator 336 may be passed through an arm guide lumen 26 for maceration of tissue T or a blood clot while a tool arm 30 is used for irrigation and aspiration. The macerator 336 macerates the tissue T to form small particles which may be more readily aspirated. Further, irrigation through the arm 30 may be used to cleanse portions of the device. For example, as illustrated in FIG. 42, the arm 30 may be steered to face the scope 28 allowing irrigation to cleanse the scope 28 thus improving viewing.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. An endoluminal tool deployment system comprising:
    an elongated main body having a distal end, a proximal end, and at least two arm guide lumens extending through at least a distal section of the elongated main body, wherein said arm guide lumens extend fully to a distal tip of the main body;
    at least two tool arms adapted to extend through the arm guide lumens of the elongated main body, said tool arms emerging from the distal tip of the main body and at least one tool arm having a distal end which is positionable relative to and independently of the elongated main body; and
    further comprising a deployment frame extending from the distal tip of the main body and having a peak portion that extends distally of the distal end of at least one of the tool arms, the frame comprising at least two supports each attached to one of the at least two tool arms so that manipulation of the deployment frame deflects the attached tool arms.

2. A system as in claim 1, wherein the elongated main body has a viewing scope lumen extending therethrough and terminating in the distal tip.

3. A system as in claim 2, wherein the distal terminations of the two arm guide lumens and the one viewing scope lumen are arranged in a generally triangular pattern on the distal tip of the main body.

4. A system as in claim 1, wherein the tool arm is axially and rotationally translatable within the arm guide lumen.

5. A system as in claim 1, wherein at least one of the tool arms has a steerable distal end which comprises a flexible tube having at least one pullwire attached thereto so that manipulation of the at least one pullwire deflects the steerable distal end.

6. A system as in claim 5, wherein at least one of the tool arms has a steerable distal end which comprises a flexible tube having shape memory material so that emergence of the steerable distal end from the distal tip of the main body allows deflection of the steerable distal end to a shape memory position.

7. A system as in claim 1, wherein the arm guide lumen extends through the distal section and terminates at a distal tip thereof.

8. A system as in claim 7, wherein the distal section of the elongated main body has a generally cylindrical exterior and wherein the arm guide lumen does not extend out of the cylindrical exterior.

9. A system as in claim 1, wherein at least the distal section of the elongated main body is steerable.

10. A system as in claim 9, wherein the distal section of the elongated main body comprises a plurality of adjacent links.

11. A system as in claim 10, further comprising a means for selectively deflecting the distal section within at least a single plane.

12. A laterally stabilized, steerable tool arm comprising:
    a shaft extending distally from an elongate main body which is adapted for endoluminal advancement, the shaft having a proximal end and a distal end, wherein a distal section of the shaft comprises a plurality of adjacent links pivotally attached by hinge structures which limit deflection of the distal section to within a single plane,
    wherein the distal section of the shaft is adapted to selectively deflect within the single plane when actuated from its proximal end such that the distal end is positioned directly in line with a longitudinal axis of the elongate main body and wherein the shaft is axially and rotationally translatable relative to the elongate main body;
    wherein the hinge structures each include a pin, wherein the pins are disposed in parallel to limit the deflection of the distal section to within the single plane;
    further comprising at least one pullwire or one pushwire for selectively deflecting the distal section, and at least one spring which is configured to straighten the distal section in opposition to the pullwire or pushwire.

13. A tool arm as in claim 12, wherein the hinge structures comprise male and female bearing surfaces which define axes, wherein the axes are disposed in parallel to limit deflection of the distal section to within the single plane.

14. A tool arm as in claim 12, wherein the distal end includes at least two steerable sections, wherein a distal-most steerable section includes a tip section which curves in a first direction and wherein an intermediate steerable section includes a base which curves in the opposite direction, where both curves are in the single plane.

15. A tool arm as in claim 14, wherein the tip section curve has a radius which is greater than that of the base curve.

16. A tool arm as in claim 12, further comprising at least one additional pullwire or pushwire for selectively deflecting the distal section.

17. A tool arm as in claim 12, wherein the adjacent links are shaped so that the steerable distal end is deflectable to form a predetermined curvature wherein the shaft is then restricted from further deflection.

18. A tool arm as in claim 12, wherein a tool deployment lumen extends through the shaft for passage of a tool therethrough.

19. A tool arm as in claim 18, wherein the tool arm further comprises a steering cuff arranged for passage of the tool therethrough so that manipulation of the tool within the steering cuff steers the distal end of the tool arm.

20. A tool arm as in claim 12, further comprising an end effector disposed on or near the distal end of the shaft.

* * * * *